(12) United States Patent
Huang et al.

(10) Patent No.: US 11,737,689 B2
(45) Date of Patent: Aug. 29, 2023

(54) PHYSIOLOGICAL SIGNAL MONITORING DEVICE

(71) Applicant: BIONIME CORPORATION, Taichung (TW)

(72) Inventors: Chun-Mu Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 282 days.

(21) Appl. No.: 16/944,582

(22) Filed: Jul. 31, 2020

(65) Prior Publication Data
US 2021/0030326 A1 Feb. 4, 2021

Related U.S. Application Data

(60) Provisional application No. 62/882,140, filed on Aug. 2, 2019.

(30) Foreign Application Priority Data

| Jan. 10, 2020 | (TW) | 109100852 |
| Jan. 10, 2020 | (TW) | 109100968 |
| Mar. 19, 2020 | (TW) | 109109241 |

(51) Int. Cl.
*A61B 5/145* (2006.01)
*A61B 5/00* (2006.01)

(52) U.S. Cl.
CPC ........ *A61B 5/14532* (2013.01); *A61B 5/0004* (2013.01); *A61B 5/14503* (2013.01);
(Continued)

(58) Field of Classification Search
CPC .............. A61B 5/14532; A61B 5/0004; A61B 5/14503; A61B 5/688; A61B 2562/166;
(Continued)

(56) References Cited

U.S. PATENT DOCUMENTS

| 8,792,955 B2 | 7/2014 | Brister et al. |
| 8,886,272 B2 | 11/2014 | Brister et al. |

(Continued)

FOREIGN PATENT DOCUMENTS

| CN | 208926382 U | 6/2019 |
| EP | 1776036 B1 | 5/2013 |

(Continued)

OTHER PUBLICATIONS

Search Report issued to European counterpart application No. 20189221.3 by the EPO dated Jan. 12, 2021.

*Primary Examiner* — Eric F Winakur
*Assistant Examiner* — Emily C Clement
(74) *Attorney, Agent, or Firm* — Perkins Coie LLP; Gautam Thatte; Viola Kung

(57) ABSTRACT

A physiological signal monitoring device includes a sensing member and a transmitter connected to the sensing member and including a circuit board that has electrical contacts, and a connecting port, which includes a socket communicated to the circuit board and a plurality of steel balls. The sensing member is removably inserted into the socket. The steel balls are electrically connected to the electrical contacts and the sensing member for enabling electric connection therebetween. Each of the steel balls is frictionally rotated by the sensing member during insertion of the sensing member into the socket and removal of the sensing member from the socket.

5 Claims, 24 Drawing Sheets

(52) U.S. Cl.
CPC ........ *A61B 5/688* (2013.01); *A61B 2562/166* (2013.01); *A61B 2562/226* (2013.01); *A61B 2562/227* (2013.01)

(58) Field of Classification Search
CPC ........ A61B 2562/226; A61B 2562/227; A61B 5/1473; A61B 5/14865; A61B 5/6848; A61B 2560/045; H01R 13/00; H01R 24/00; H01R 3/00; H01R 4/00; H01R 12/87; H01R 2201/12; H01R 11/00; H01R 12/50; H01R 12/70; H01R 12/88; H01R 2201/00; H01R 25/00; H01R 27/00; H01R 31/00; H01R 33/00; H01R 35/00; H01R 39/00; H01R 41/00; H01R 43/00; H01R 9/00; A61H 2230/202; A63B 2230/202; A61M 2230/201

See application file for complete search history.

(56) References Cited

U.S. PATENT DOCUMENTS

| | | | |
|---|---|---|---|
| 9,078,607 B2 | 7/2015 | Heller et al. | |
| 10,327,638 B2 | 6/2019 | Brister et al. | |
| 2008/0021491 A1 | 1/2008 | Freeman et al. | |
| 2010/0198034 A1 | 8/2010 | Thomas et al. | |
| 2010/0233896 A1* | 9/2010 | Dilmaghanian | H01R 13/187 439/669 |
| 2010/0312188 A1 | 12/2010 | Robertson et al. | |
| 2012/0073966 A1 | 3/2012 | Hsu et al. | |
| 2012/0302853 A1 | 11/2012 | Chen et al. | |
| 2013/0089919 A1 | 4/2013 | Wu et al. | |
| 2013/0267811 A1 | 10/2013 | Pryor et al. | |
| 2016/0015267 A1 | 1/2016 | Bernstein et al. | |
| 2016/0157759 A1 | 6/2016 | Yang | |
| 2017/0188910 A1 | 7/2017 | Halac et al. | |
| 2017/0188911 A1 | 7/2017 | Halac et al. | |
| 2017/0188912 A1 | 7/2017 | Halac et al. | |
| 2017/0258402 A1 | 9/2017 | Acquista et al. | |
| 2017/0290546 A1 | 10/2017 | Antonio et al. | |
| 2019/0074644 A1* | 3/2019 | White | H01R 24/58 |
| 2019/0320956 A1 | 10/2019 | Pryor et al. | |

FOREIGN PATENT DOCUMENTS

| | | |
|---|---|---|
| WO | 2008/105768 A1 | 9/2008 |
| WO | 2008105768 A1 | 9/2008 |
| WO | 2011/041463 A2 | 4/2011 |
| WO | 2011041463 A2 | 4/2011 |
| WO | 2012/097891 A1 | 7/2012 |
| WO | 2012097891 A1 | 7/2012 |
| WO | 2016/019250 A1 | 2/2016 |
| WO | 2016019250 A1 | 2/2016 |
| WO | 2016/090189 A1 | 6/2016 |
| WO | 2016090189 A1 | 6/2016 |
| WO | 2017/004531 A1 | 1/2017 |
| WO | 2017004531 A1 | 1/2017 |
| WO | 2017/116915 A1 | 7/2017 |
| WO | 2017116915 A1 | 7/2017 |

\* cited by examiner

PHYSIOLOGICAL SIGNAL MONITORING DEVICE

CROSS-REFERENCE TO RELATED APPLICATION

This application claims priorities of U.S. Provisional Patent Application No. 62/882,140, filed on Aug. 2, 2019, Taiwanese Patent Application No. 109109241, filed on Mar. 19, 2020, Taiwanese Patent Application No. 109100968, filed on Jan. 10, 2020, and Taiwanese Patent Application No. 109100852, filed on Jan. 10, 2020.

FIELD

The disclosure relates to a sensor, and more particularly to a physiological signal monitoring device.

BACKGROUND

Referring to FIG. 23, a conventional sensing device 900 disclosed in U.S. Pat. No. 7,899,511 includes a base 92, an adhesive base 91 that is adapted for adhering the base 92 onto a host's skin (not shown), a biosensor 93 that is mounted in the base 92, and a transducer 94 that is mounted to the base 92 and that is connected to the biosensor 93. The biosensor 93 is inserted beneath the host's skin for measuring a physiological signal corresponding to the blood glucose concentration level, and the transducer 94 receives the physiological signal from the biosensor 93 and forwards the physiological signal to an external device (not shown).

Furthermore, referring to FIG. 24, the biosensor 93 includes a fixed seat 931, an elongated sensing member 932 that is fixedly mounted to the fixed seat 931, and two contactor heads 933 that are fixedly mounted to the fixed seat 931 and that are in contact with the sensing member 932. When the transducer 94 covers the base 92 to be mounted thereto, contact points (not shown) at a bottom end of the transducer 94 are to be in direct contact with the contactor heads 933 for enabling electric connection between the transducer 94 and the sensing member 932. However, as the transducer 94 and the sensing members 932 are spaced apart in a coupling direction while the contactor heads 933 extends in the same direction for enabling the electric connection therebetween, the thickness of each of the contactor heads 933 (length in the coupling direction) cannot be smaller than the distance between the transducer 94 and the sensing member 932. As such, minimum thickness restriction to the contactor heads 933 made it difficult to reduce the overall thickness of sensing device 900. In addition, the contactor heads 933 may not be able to properly enable electric connection between the biosensor 93 and the transducer 94 due to manufacturing errors, such as misalignment of the contactor heads 933, or the contactor heads 933 having the thickness different from the distance between the transducer 94 and the sensing member 932.

SUMMARY

Therefore, an object of the disclosure is to provide a physiological signal monitoring device that can alleviate the drawbacks of the prior art.

According to an aspect of the disclosure, the physiological signal monitoring device is for sensing a physiological signal in an analyte of a host, and includes a sensing member and a transmitter. The sensing member includes a signal sensing end adapted to be inserted underneath a skin of the host to sense the physiological signal, and a signal output end for outputting the physiological signal. The transmitter is connected to the sensing member for receiving, processing and transmitting the physiological signal, and includes a circuit board and a connecting port. The circuit board has a plurality of electrical contacts. The connecting port is connected to the circuit board and has a socket which is communicated to the circuit board, and a plurality of conducting balls which are received within the connecting port. The sensing member is removably inserted into the socket. Each of the steel balls has one side electrically connected to a respective one of the electrical contacts of the circuit board and another side electrically connected to the signal output end of the sensing member for electric connection between the respective one of the electrical contacts and the signal output end. Each of the steel balls is frictionally rotated by the sensing member during insertion of the sensing member into the socket and removal of the sensing member from the socket.

According to another aspect of the disclosure, the physiological signal monitoring device is for sensing a physiological signal in an analyte of a host, and includes a sensing member and a transmitter. The sensing member includes a signal sensing end adapted to be inserted underneath a skin of the host to sense the physiological signal, and a signal output end for outputting the physiological signal. The transmitter is connected to the sensing member for receiving, processing and transmitting the physiological signal, and includes a circuit board and a connecting port. The circuit board has a plurality of electrical contacts. The connecting port is connected to the circuit board and has a socket which is communicated to the circuit board, and a plurality of conducting balls which are received within the connecting port. The sensing member is removably inserted into the socket. Each of the steel rings has one side electrically connected to a respective one of the electrical contacts of the circuit board and another side electrically connected to the signal output end of the sensing member for electric connection between the respective one of the electrical contacts and the signal output end. Each of the steel rings is frictionally rotated by the sensing member during insertion of the sensing member into the socket and removal of the sensing member from the socket.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
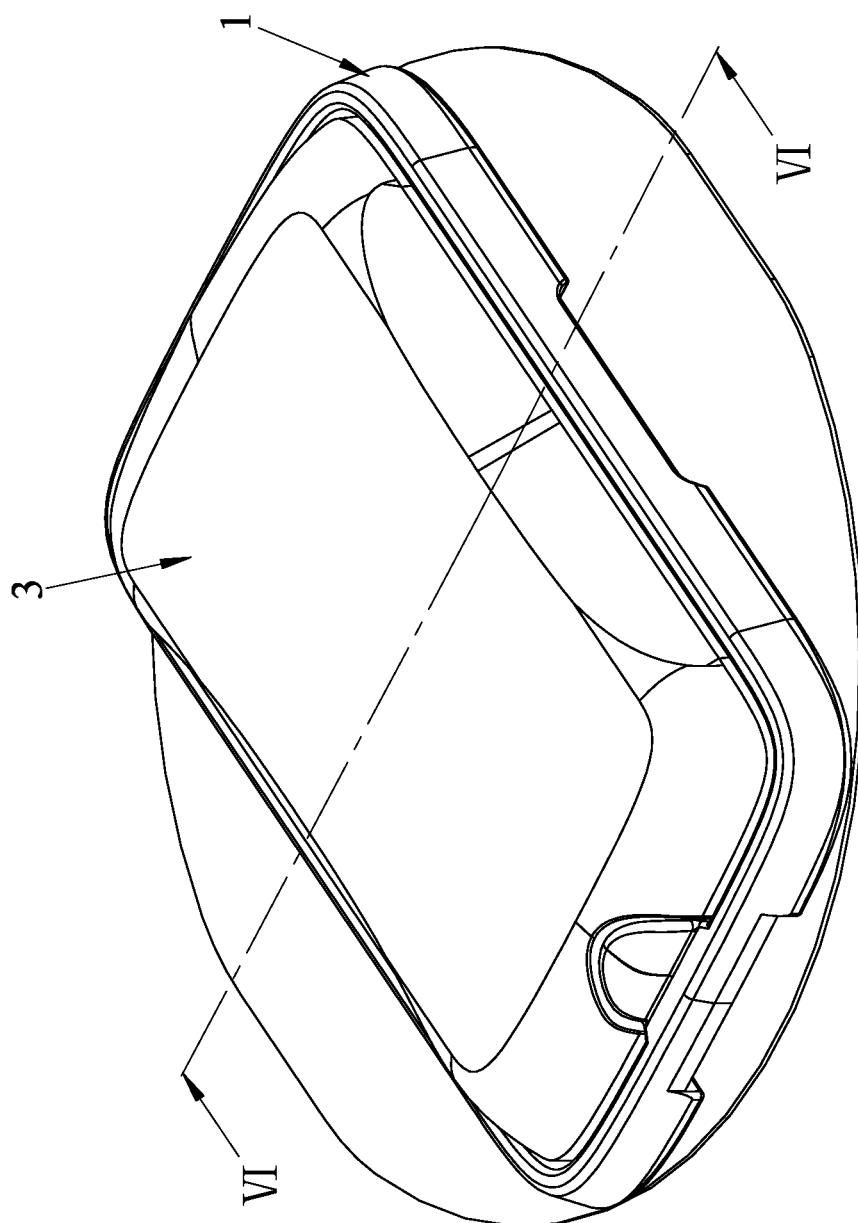
FIG. 1 is a perspective view of a first embodiment of a physiological signal monitoring device according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

In addition, in the description of the disclosure, the terms "up", "down", "top", "bottom" are meant to indicate relative position between the elements of the disclosure, and are not meant to indicate the actual position of each of the elements in actual implementations. Similarly, various axes to be disclosed herein, while defined to be perpendicular to one another in the disclosure, may not be necessarily perpendicular in actual implementation.

Referring to FIGS. 1 to 7, a first embodiment of the physiological signal monitoring device according to the disclosure is adapted to be mounted to a skin surface of a host (not shown), and is adapted for measuring at least one analyte of the host and for sending a corresponding type of physiological signal. In this embodiment, the physiological signal monitoring device is for measuring the blood glucose concentration in the interstitial fluid (ISF) of the host, and is meant to be mounted to the skin surface for two weeks, but is not restricted to such.

Referring back to FIGS. 1 and 2, the physiological signal monitoring device includes a base 1 that is adapted to be mounted to the skin surface of the host, a biosensor 2 that is mounted to the base 1 and that is adapted to be partially inserted underneath the skin surface of the host, and a transmitter 3 that covers and is removably coupled to the base 1 in a direction of a first axis (D1) and that is connected to the biosensor 2. The biosensor 2 is adapted for measuring at least one analyte of the host and for sending a corresponding physiological signal to the transmitter 3, while the transmitter 3 receives, processes, and outputs the physiological signal to an external device (not shown) for monitoring purposes. When the physiological signal monitoring device is to be replaced after a prolonged period of use, the transmitter 3 is permitted to be separated from the biosensor 2 and the base 1 to be reused with a new set of the base 1 and biosensor 2.

The base 1 includes a base body 11, and an adhesive pad 16 that is mounted to a bottom surface 116 (see FIG. 6) of the base body 11 and that is permitted for attaching the base body 11 to the skin surface of the host. The biosensor 2 includes a fixed seat 21 that is mounted to the base body 11, and a sensing member 22 that is mounted to the fixed seat 21 and that extends through the base body 11. The fixed seat 21 is mounted between the transmitter 3 and the base 1 when the transmitter 3 is coupled to the base 1.

The fixed seat 21 has a bottom surface 211 and a top surface 212. The sensing member 22 has a signal sensing end 222 that is adapted to be inserted underneath the skin surface of the host for measuring the physiological signal of the host, and a signal output end 221 that is adapted to output the physiological signal received from the signal sensing end 222. The signal sensing end 222 protrudes from the bottom surface 211 of the fixed seat 21, and the signal output end 221 protrudes from the top surface 212 of the fixed seat 21.

Figure 2:
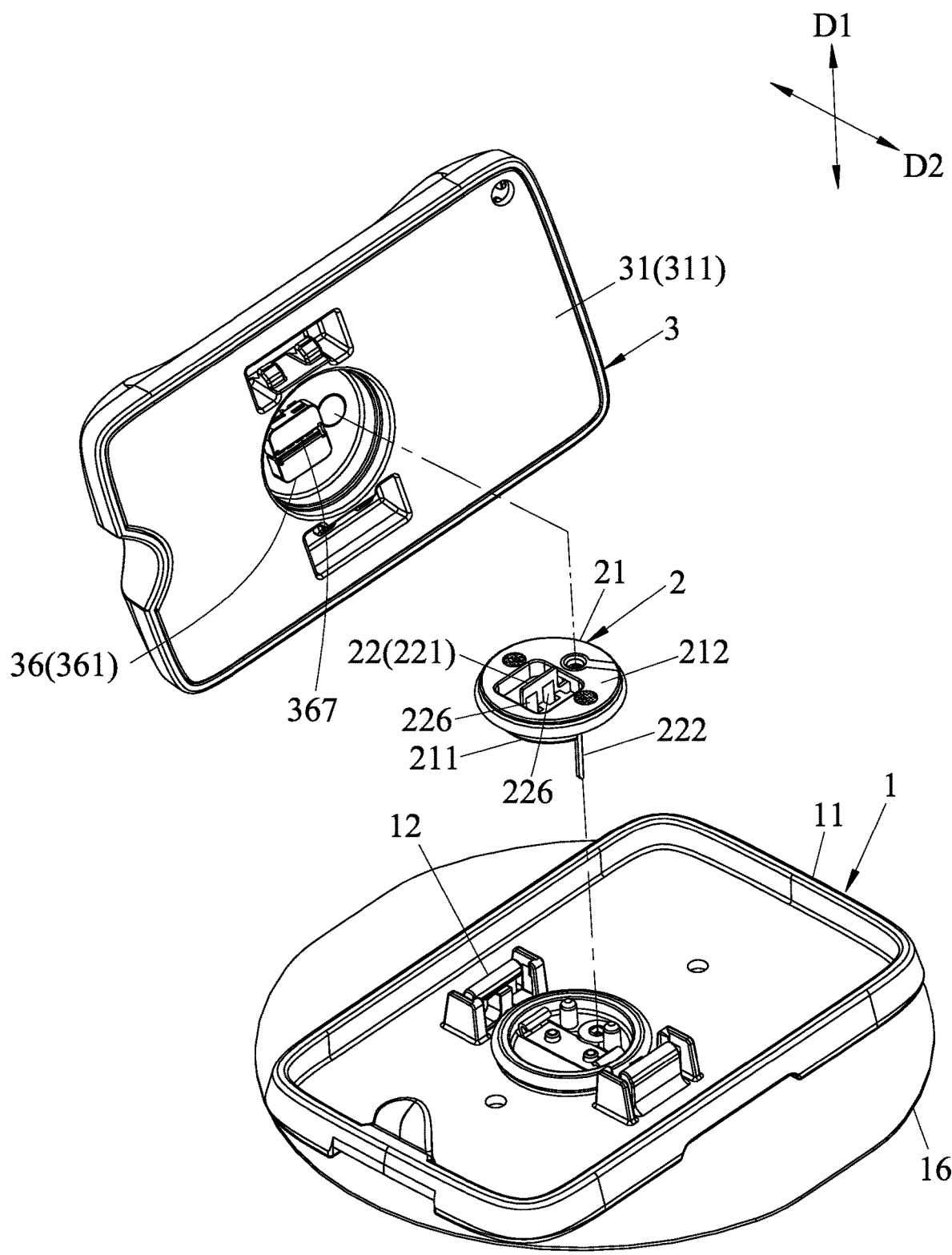
FIG. 2 is an exploded perspective view of the first embodiment.
Figure 3:
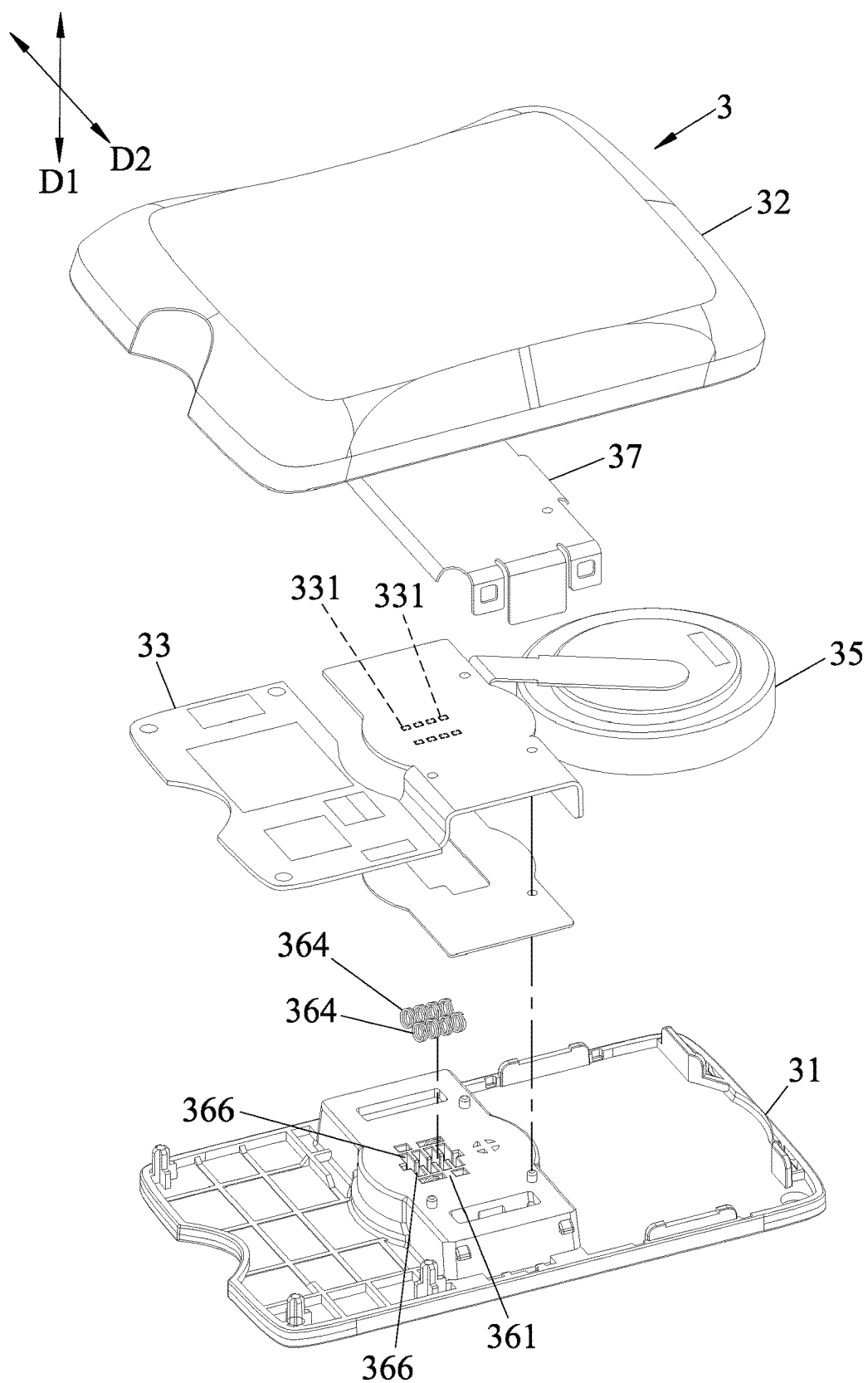
FIG. 3 is an exploded perspective view of a transmitter of the first embodiment.
Figure 4:
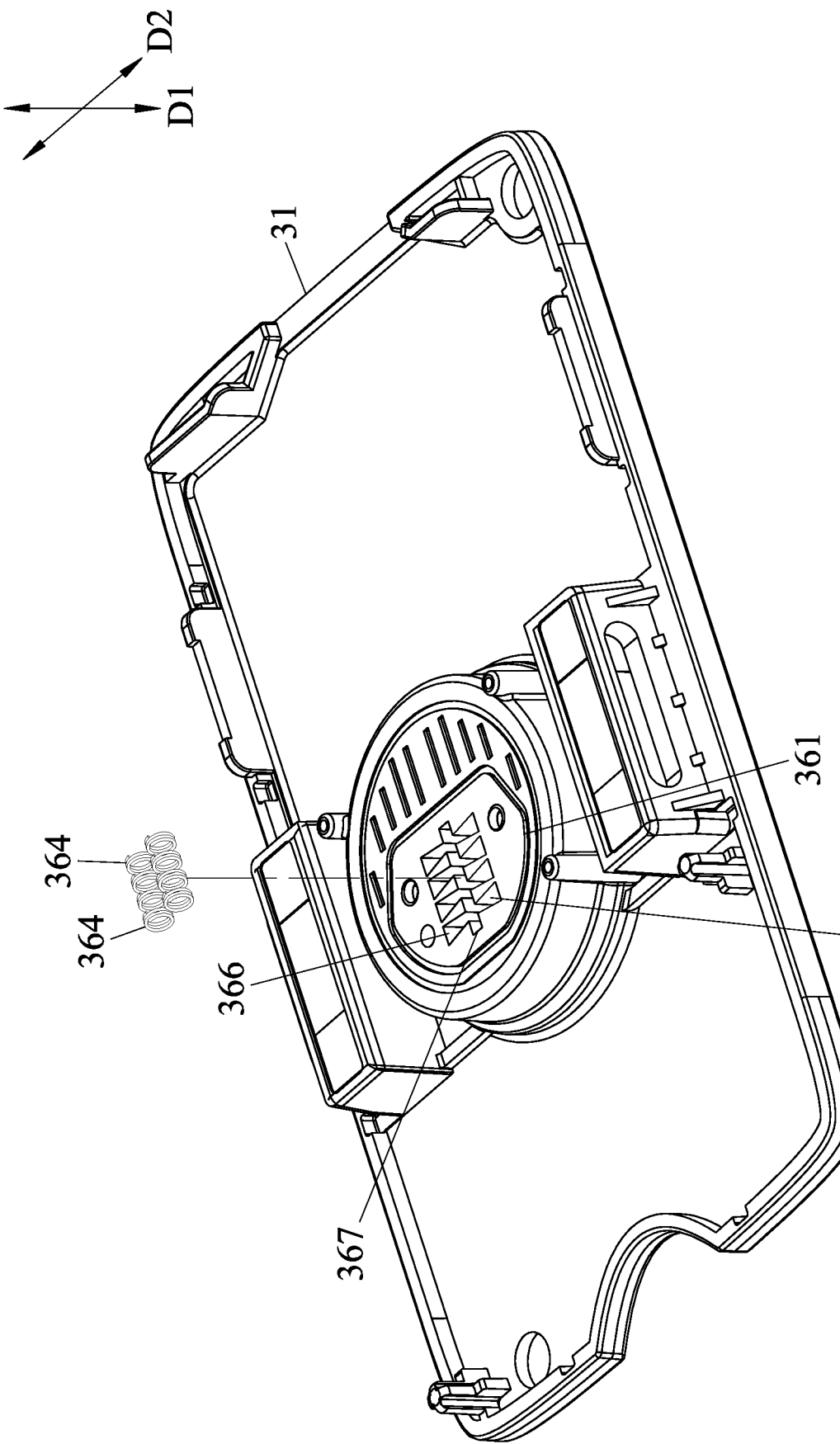
FIG. 4 is a partly exploded perspective view of a bottom casing and a connecting port of the transmitter of a modification the first embodiment.
Figure 5:
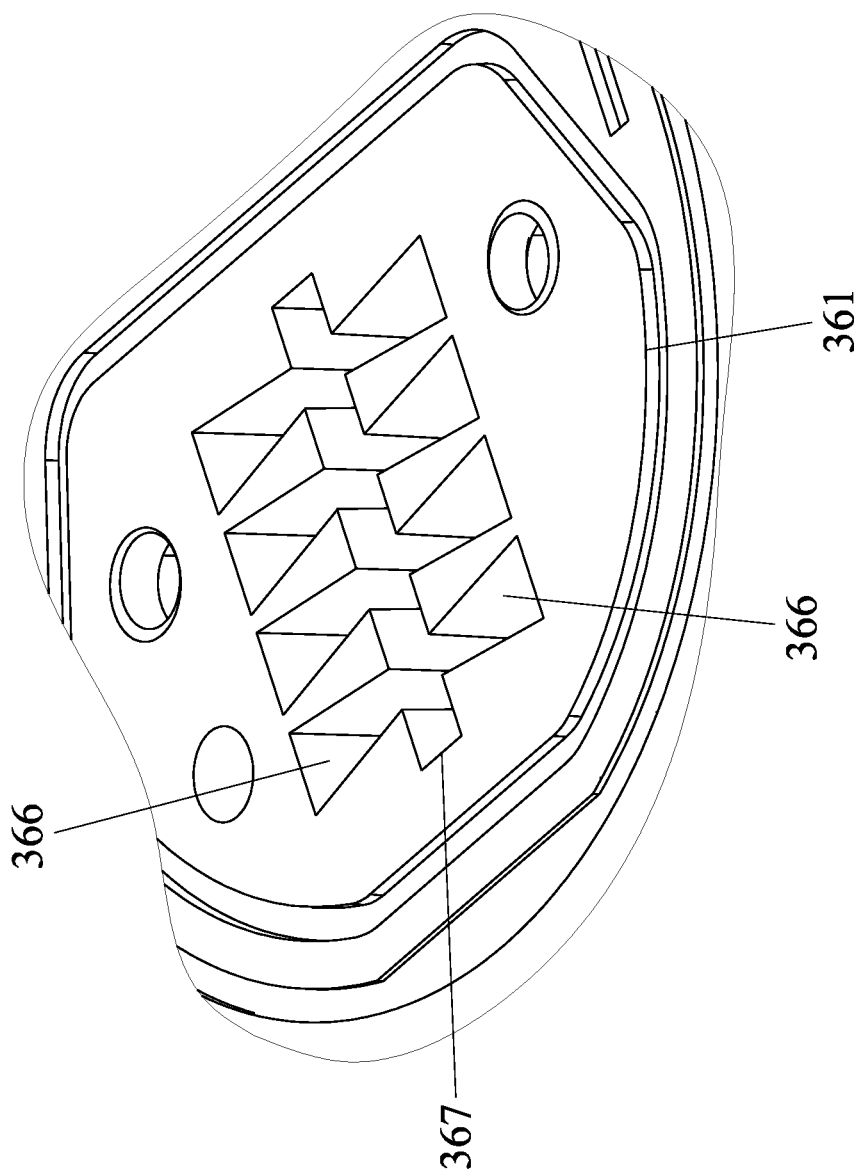
FIG. 5 is a fragmentary and enlarged perspective view of the connecting port in FIG. 4.
Figure 6:
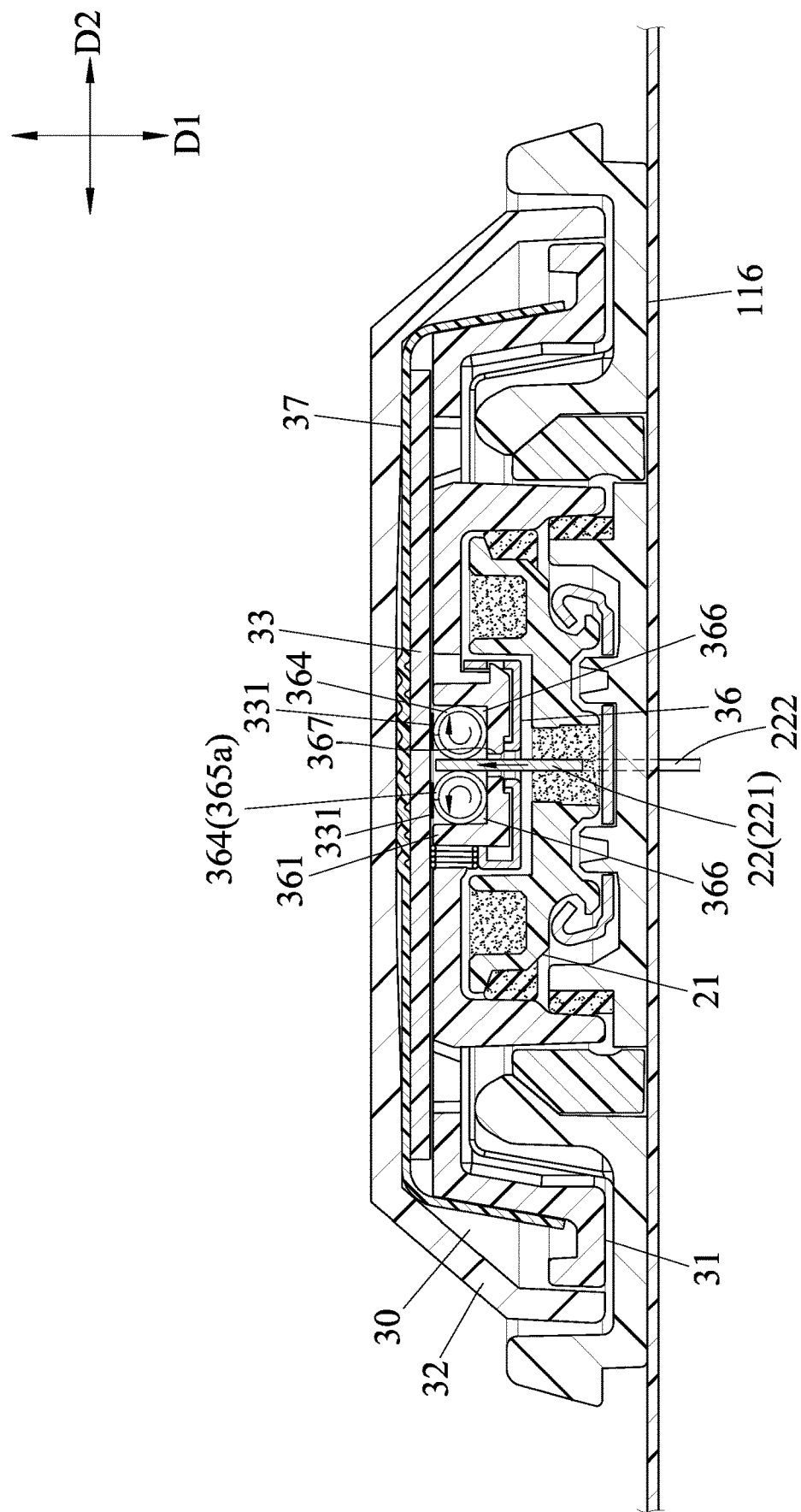
FIG. 6 is a fragmentary sectional view taken along line VI-VI in FIG. 1.
Figure 7:
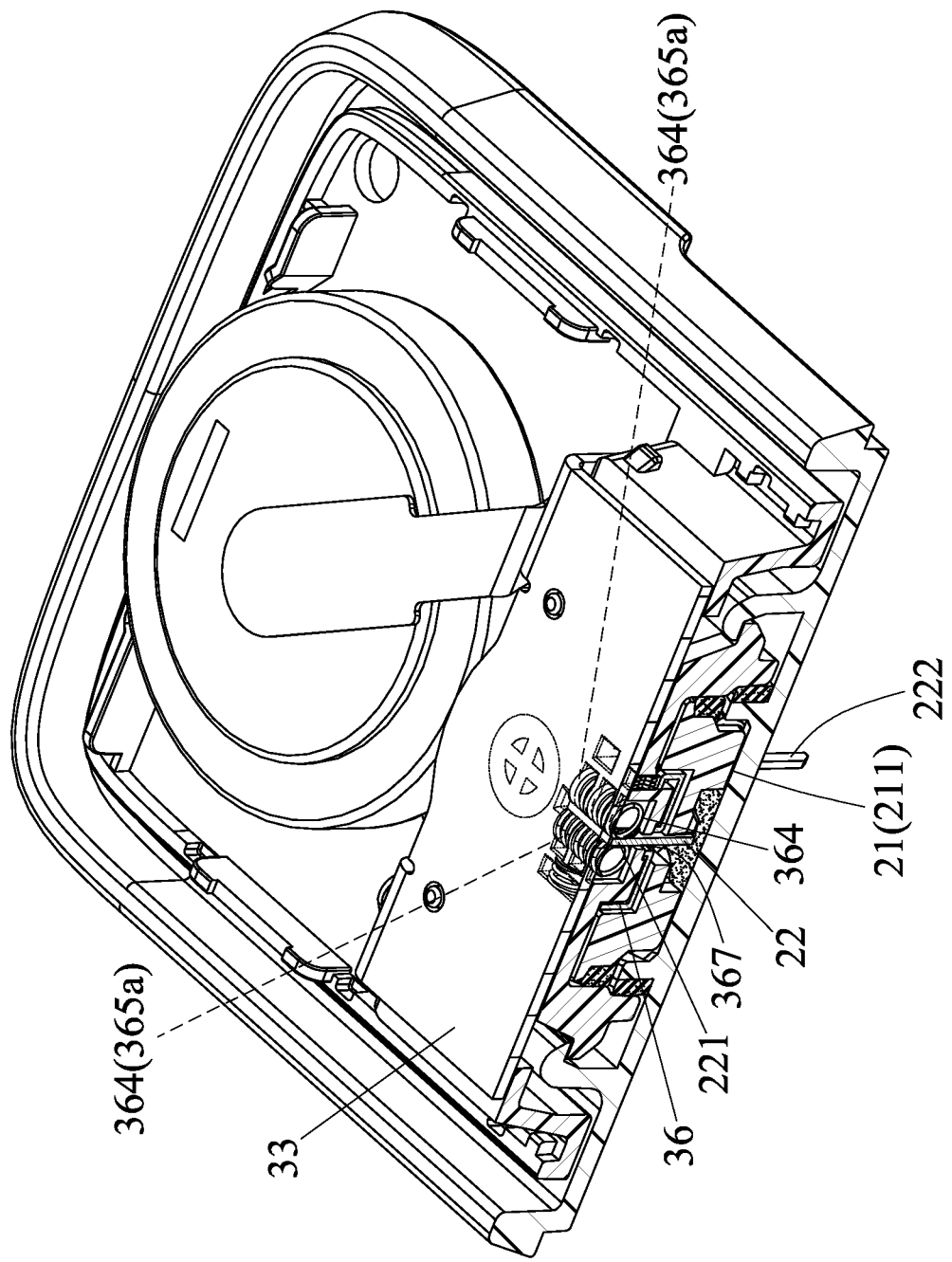
FIG. 7 is a cutaway perspective view of the first embodiment.
Figure 11:
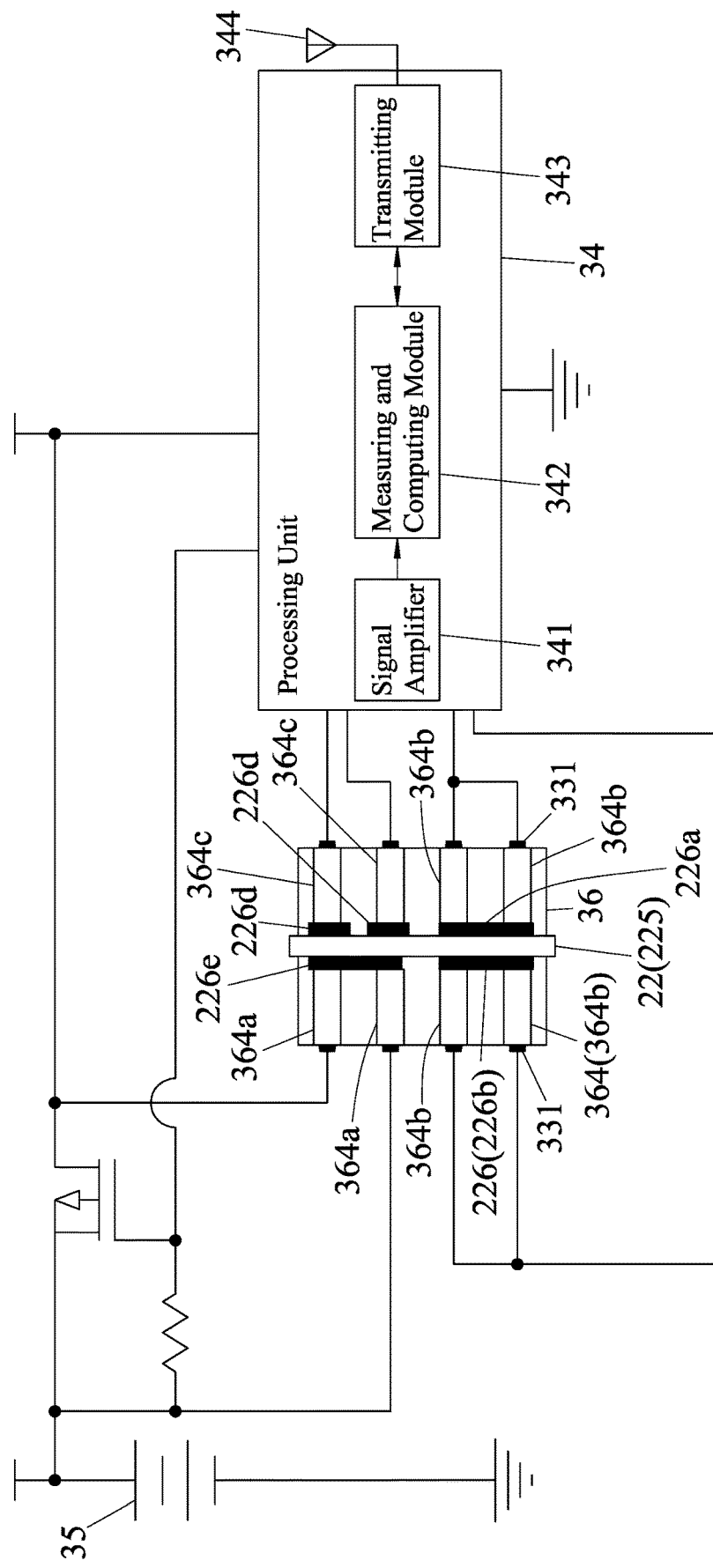

Referring to FIGS. 2 and 11, the sensing member 22 includes a base board 225, a plurality of electrodes 226 mounted to a surface of the base board 225, and an analyte sensing layer (not shown) that covers the electrodes 226 and the surface of the base board 225. The analyte sensing layer is provided for reacting with the at least one analyte of the host, and the electrodes 226 includes signal receiving electrodes that detect outcome of the reaction, and signal sending electrodes that generate an electric signal indicating the outcome of the reaction. In this embodiment, the electric signal is the physiological signal that indicates glucose levels in the interstitial fluid. Specific roles of the electrodes 226 will be elaborated later.

Referring back to FIGS. 2, 3 and 6, the transmitter 3 includes a bottom casing 31 that is proximate to the base body 11, a top casing 32 that is mounted to the bottom casing 31 to define an inner space 30, a circuit board 33 that is disposed in the inner space 30, a processing unit 34 (see FIGS. 10 and 11) that is mounted to the circuit board 33, a battery 35 that is disposed in the inner space 30, and a connecting port 36 that is connected to a bottom surface of the circuit board 33 and that extends outwardly from the inner space 30 toward the base body 11.

The circuit board 33 is permitted to be printed circuit board (PCB) or flexible print circuit (FPC), and is fixedly positioned to the bottom casing 31 via a supporting member 37, which may be made of a metal plate. The circuit board 33 has a plurality of electrical contacts 331 that correspond in position to the connecting port 36. In this embodiment, the number of the electrical contacts 331 is eight. The processing unit 34 is provided for receiving, processing, and sending the physiological signal, and is connected to the electrical contacts 331. The battery 35 is connected to the electrical contacts 331 of the circuit board 33.

Referring back to FIGS. 3, 6 and 7, the connecting port 36 includes a port casing 361 that is mounted to a bottom surface of the circuit board 33 and that extends downwardly toward a bottom surface 311 of the bottom casing 31 in the direction of the first axis (D1), and a plurality of spaced-apart conducting members 364 that are received within the port casing 361. In this embodiment, the number of the conducting members 364 is eight.

The port casing 361 is formed with a plurality of grooves 366 open toward the circuit board 33 and respectively receiving the conducting members 364 therein, and a socket 367 that extends toward the base body 11 in the direction of the first axis (D1) and that is communicated to the grooves 366. The conducting members 364 are respectively and rotatably received within the grooves 366. The socket 367 is provided to hold the signal output end 221 of the sensing member 22.

Referring back to FIGS. 4 and 5, in a modification of the first embodiment, a cross section of an outer periphery of the grooves 336 perpendicular to the first axis (D1) is substantially dovetail-shaped, and each of the grooves 336 tapers toward the socket 367 for preventing each of the conducting members 364 from escaping the respective one of the grooves 336.

The conducting members 364 are elastic, and are disposed at two opposite sides of the socket 367. In this embodiment, the conducting members 364 are conducting coil springs. Each of the conducting members 364 contacts with the circuit board 33 at one side along with a first direction, and contacts with the sensing member 22 at another side along a second direction wherein the first direction is nonparallel to the second direction. Therefore, the electric connection between the electrical contacts 331 of the circuit board 33 and the signal output end 221 of the sensing member 22 is provide when the sensing member 22 is inserted into the socket 367. Specifically, each of the conducting members 364 has one side that is in contact with (and electrically connected to) a respective one of the electrical contacts 331 of the circuit board 33 in the direction of the first axis (D1) (i.e., the first direction) and another side that is in contact with (and electrically connected to) the electrodes 226 on the signal output end 221 of the sensing member 22 in a direction of a second axis (D2) (i.e., the second direction) for positioning the sensing member 22 when it is inserted into the socket 367 and for enabling electric connection between the electrical contacts 331 of the circuit board 33 and the signal output end 221 of the sensing member 22. In this embodiment, the first and second axes (D1, D2) are substantially perpendicular to each other, but may not be restricted as such in other embodiments. The conducting coil springs have high degrees of freedom such that each of the conducting members 364 is rotated relative to the grooves 366 during insertion of the sensing member 22 into the socket 367 and removal of the sensing member 22 from the socket 367 along the first axis (D1), thereby reducing friction between the socket 367 and the sensing member 22 and facilitating the reuse of the transmitter 3.

It should be noted that, in this embodiment, each of the conducting members 364 has one end welded to the port casing 361 so that one end of each of the conducting members 364 is fixed on the respective one of the grooves 366. In addition, as the conducting members 364 are conducting coil springs, each of the conducting members 364 has the following properties: the wire diameter thereof is smaller than 1 millimeter (mm), preferably 0.1 mm; the outer diameter thereof ranges from 0.5 mm to 1.8 mm, preferably 1.1 mm; the free length thereof ranges from 0.2 mm to 0.8 mm, preferably 0.44 mm to 0.56 mm. Each of the conducting members 364 has a helical portion 365a with two to six turns (three turns in this embodiment), thereby providing multi-point contacts with the respective one of the electrical contacts 331 of the circuit board 33 and the signal output end 221 of the sensing member 22. It should be noted that, parameters such as the wire diameter and the number of turns of each of the conducting members 364 are designed in consideration to the elasticity of the conducting members 364, and the outer diameter and the free length of each of the conducting members 364 are designed in such a way that each of the conducting members 364 is slightly larger than a space of the respective one of the grooves 366, so that the conducting members 364 are in stable contact with the electrical contacts 331 of the circuit board 33 and the electrodes 226 on the signal output end 221 of the sensing member 22 (see FIGS. 2 and 11).

Figure 8:
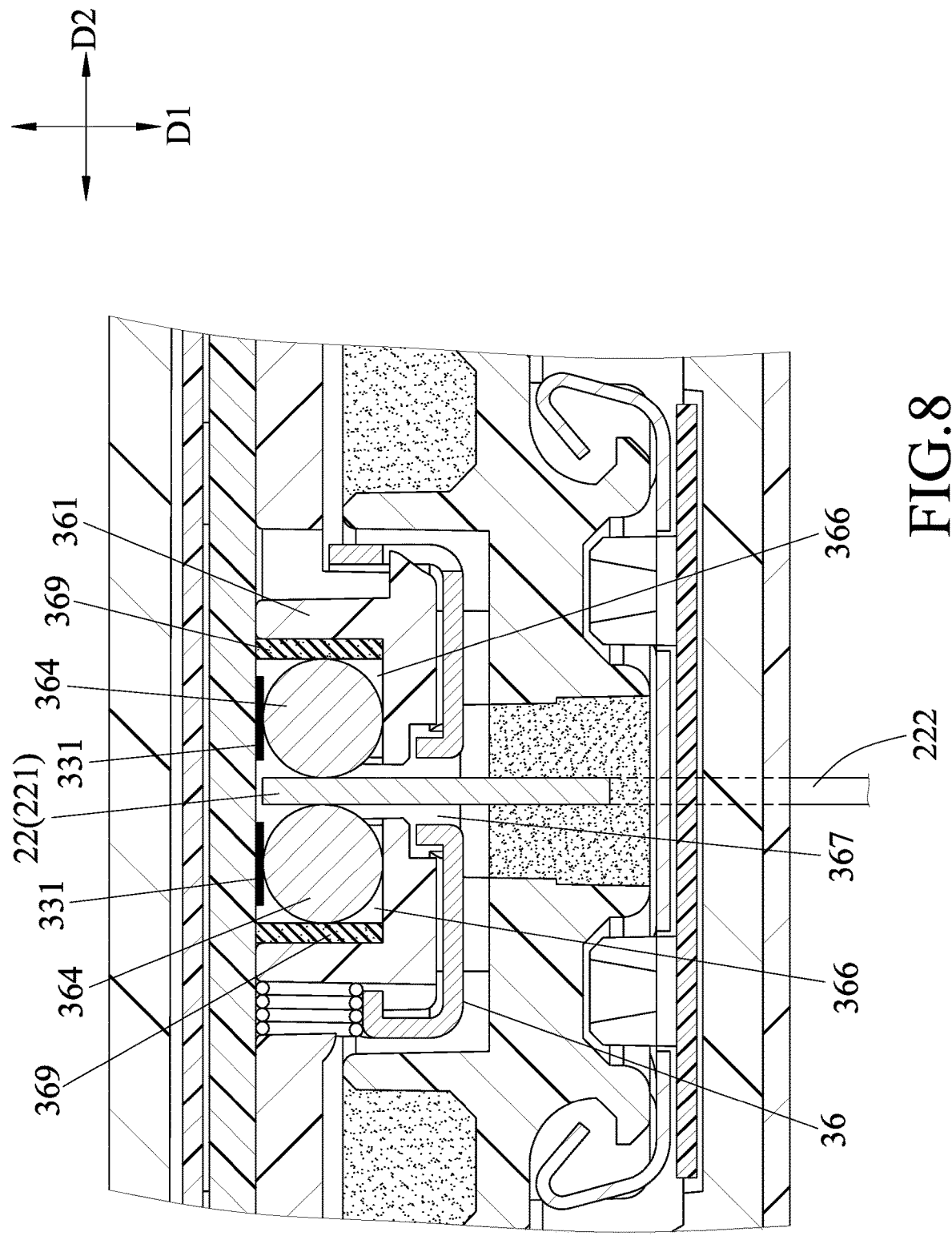
FIG. 8 is a fragmentary sectional view of another modification of the first embodiment.

Referring to FIG. 8, in another modification of the first embodiment, the conducting members 364 of the connecting port 36, which were originally conductive coil springs in the first embodiment, are steel balls or steel rings (i.e., rigid components) instead. In addition, the connecting port 36 further includes a plurality of elastic members 369, each of which is mounted in the respective one of the grooves 366 and is mounted between the port casing 361 and a respective one of the conducting members 364. The elastic members 369 are made of elastic materials such as rubber, and each of the conducting members 364 has one side contacted with the respective elastic member 369 and another side contacted with the electrodes 226 of the the signal output end 221 along an axis parallel to the second axis (D2). Overall, the conducting members 364 in this modification functions similarly to that of the first embodiment: enabling electric connection between the electrical contacts 331 and the signal output end 221, and being frictionally moved by the sensing member 22 to rotate in the grooves 366. The elastic members 369 ensure that the conducting members 364 are in stable contact with the sensing member 22 and the circuit board 33 along the directions parallel to the first axis (D1) and the second axis (D2) respectively.

Figure 9:
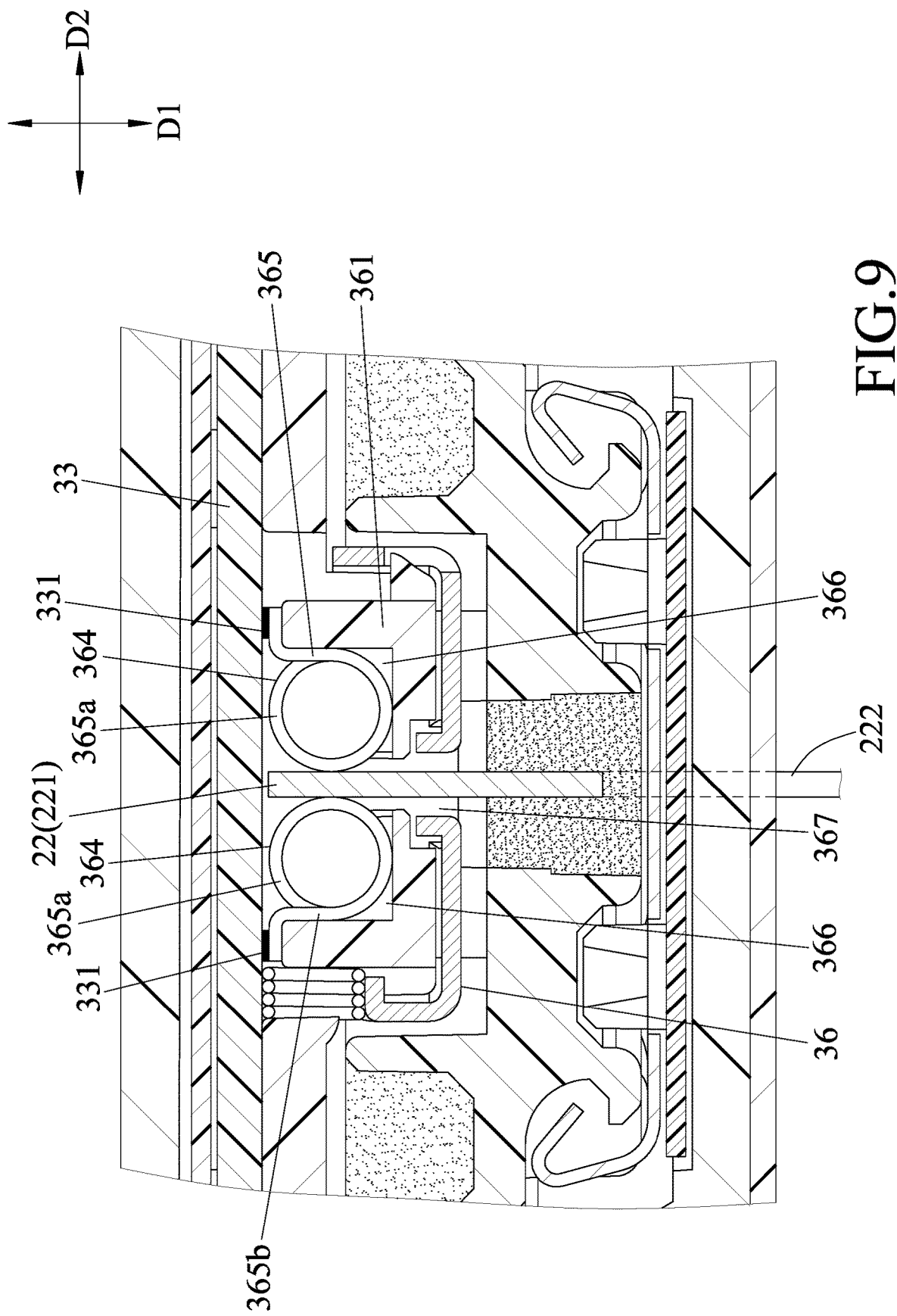
FIG. 9 is a fragmentary sectional view of yet another modification of the first embodiment.

Referring to FIG. 9, in yet another modification of the first embodiment, the conducting members 364 are conducting coil strings, each of which has an extended section 365b that extends along an inner surface of the port casing 361 toward the circuit board 33, and that is connected to the respective one of the electrical contacts 331 in the direction of the first axis (D1).

Figure 10:
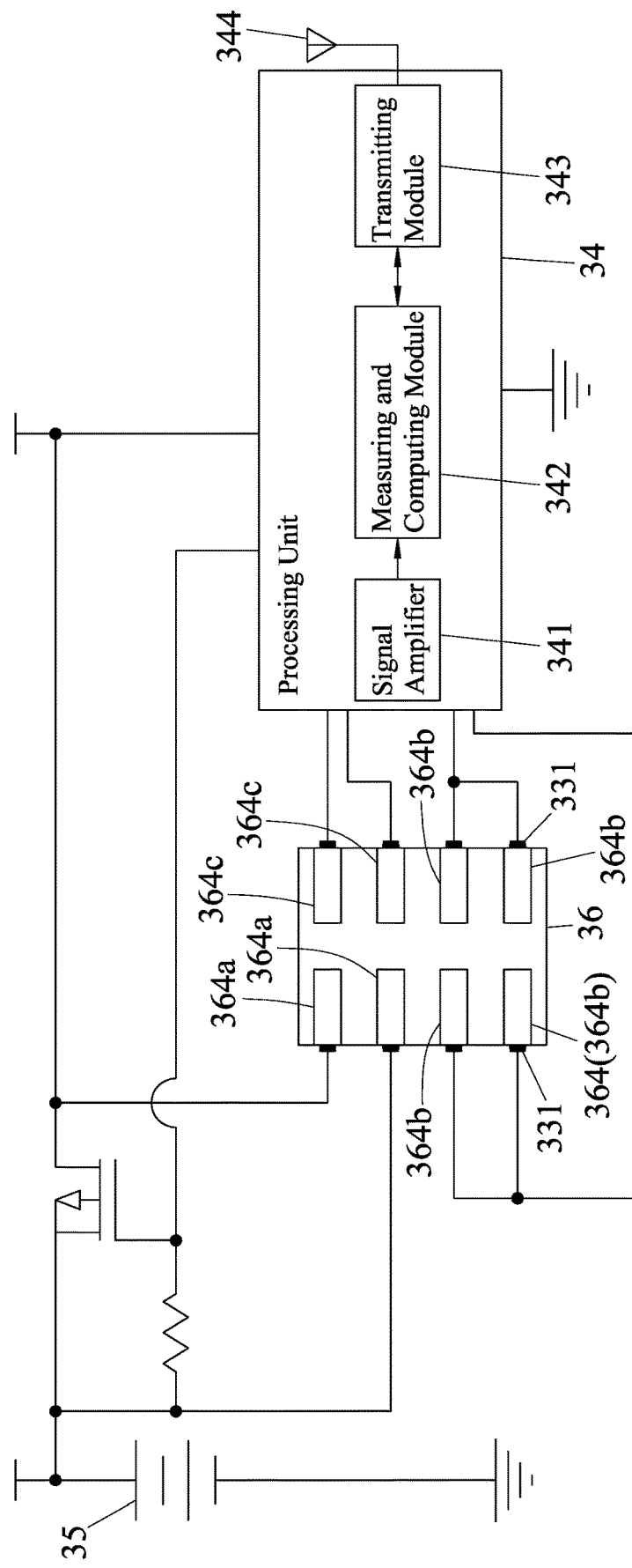
FIGS. 10 and 11 circuit diagrams of the first embodiment, respectively illustrating the transmitter before and after being coupled to a biosensor.

Referring to FIGS. 10 and 11, in the first embodiment, the processing unit 34 receives the electric signal from the sensing member 22 and sends a corresponding physiological signal. The processing unit 34 includes a signal amplifier 341 receiving and amplifying the electric signal, a measuring and computing module 342 that converts the amplified electric signal sequentially into a physiological signal corresponding to the glucose level, and a transmitting module 343 that sends the physiological digital signal to an external device (not shown) via an antenna 344. It should be noted that, in the disclosure, the abovementioned physiological signal corresponding to the glucose level is electric current.

As previously mentioned, the number of the conducting members 364 is eight in this embodiment. The conducting members 364 are conducting coil springs and include two power-supplying conducting members 364a, four sensing conducting members 364b, and two transmitting conducting members 364c. The electrodes 226 of the sensing member 22 are in contact with the conducting members 364 to be respectively and electrically connected to the electrical contacts 331 of the circuit board 33 for the purposes of supplying power, sensing and transmitting data.

The power-supplying conducting members 364a and the electrodes 226 cooperatively forma switch. The sensing conducting members 364b are connected to the processing unit 34. The transmitting conducting members 364c are connected to the processing unit 34 as well, and transmit data to the external device via the transmitting module 343 and the antenna 344. In this embodiment, type of data transmission may be wireless transmission (Bluetooth, Wifi, NFC), but may be wired transmission (USB cable) in other embodiments.

In this embodiment, the number of the electrodes 226 of the sensing member 22 is five. The electrodes 226 include a working electrode 226a, a reference electrode 226b, a power-supplying electrode 226e, and two electrical contact sections 226d.

When the sensing member 22 is not inserted into the socket 367 of the connecting port 36, the switch formed by the conducting members 364a is in an open circuit state, so that the battery 35 is in a non-power supplying state.

When the sensing member 22 is inserted into the socket 367, the power-supplying electrode 226e of the sensing member 22 is in contact with the power-supplying conducting members 364a to be electrically connected with the electrical contacts 331 of the circuit board 33, such that the switch is in a closed circuit state and the battery 35 is switched to a power supplying state for supplying power to the sensing member 22 and the processing unit 34 for performing measurement of the analyte. At the same time, each of the working and reference electrode 226a, 226b is in contact with corresponding two of the sensing conducting members 364b to be electrically connected to the electrical contacts 331 of the circuit board 33, such that the processing unit 34 receives, processes, and sends the physiological signal to the external device. The electrical contact sections 226d are permitted to be respectively and electrically connected to the transmitting conducting members 364c. In this embodiment, the electrical contact sections 226d has signal receiving and signal sending electrodes.

Figure 12:
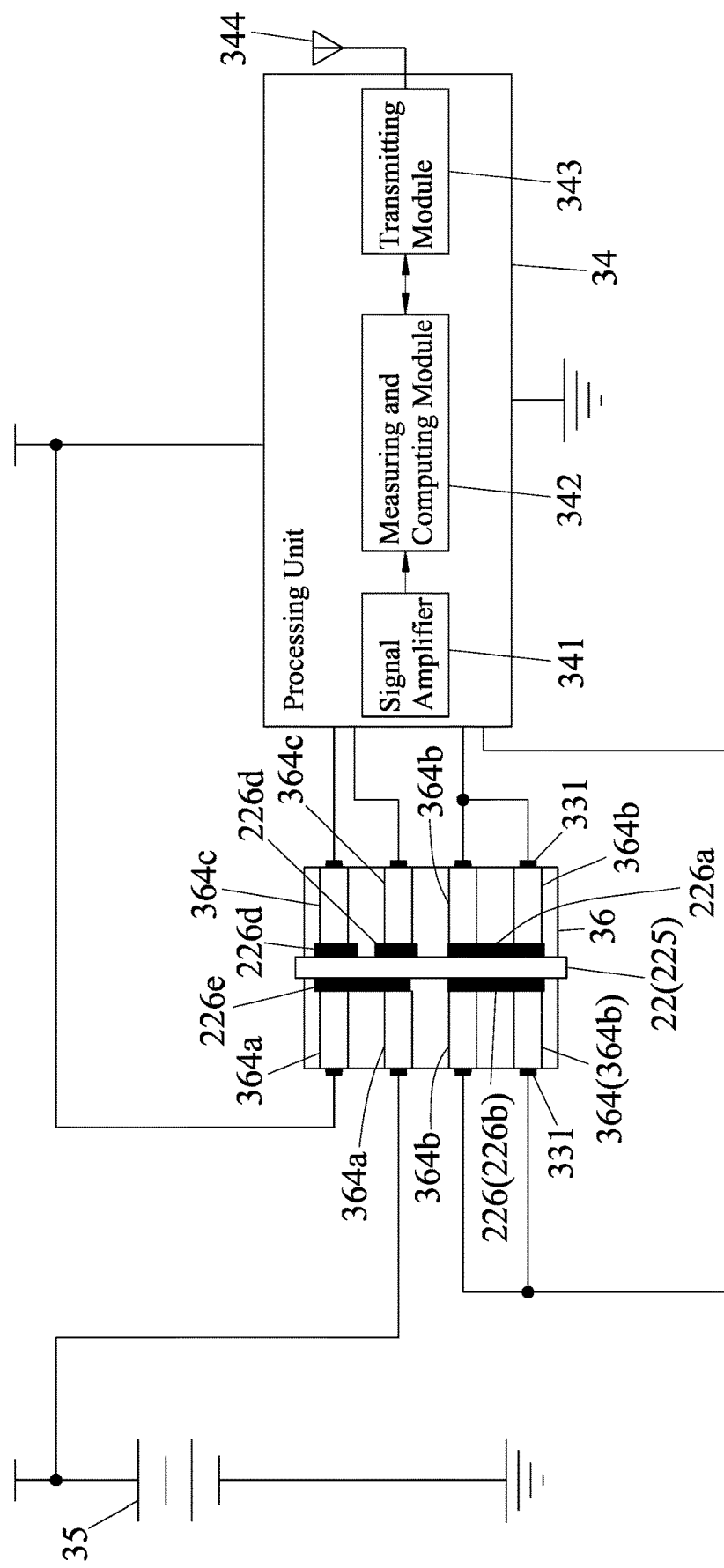
FIGS. 12 to 14 are circuit diagrams of various modifications of a sensing member and a connecting port of the first embodiment.

A circuit layout of the transmitter 3 can be modified according to the various requirement of the product. For example, referring to FIG. 12, the sensing member 22 begins measurement of the physiological signal of the host without power control by the processing unit 34 when the sensing member 22 is inserted into the socket 367. The circuit concerning to the power supply can be rearranged in other embodiments, so there is no more detailed description herein.

In addition, the socket 367 of the connecting port is further adapted for additional transmission device (not shown) or charging device (not shown) to be inserted thereinto. For example, after the transmitter 3 is manufactured (before being connected to the biosensor 2 and the base 1), a connector (or an electrode) of the additional transmission device may be inserted into the socket 367 to provide electric connection and data transmission between the processing unit 34 and the additional transmission device through the transmitting conducting members 364c. In other words, in this embodiment, the transmitting conducting members 364c are permitted to be electrically connected to the additional transmission device for exchanging data (default data or calibration data) before the transmitter 3 is connected to the biosensor 2 and the base 1. Furthermore, when the transmitter 3 is uncoupled from the biosensor and the base 1 for repeated use, the charging device may be inserted into the socket 367 to recharge the transmitter 3 through the power-supplying conducting members 364a, which electrically interconnect the electrical contacts 331 of the circuit board 33 and the charging device.

Figure 13:
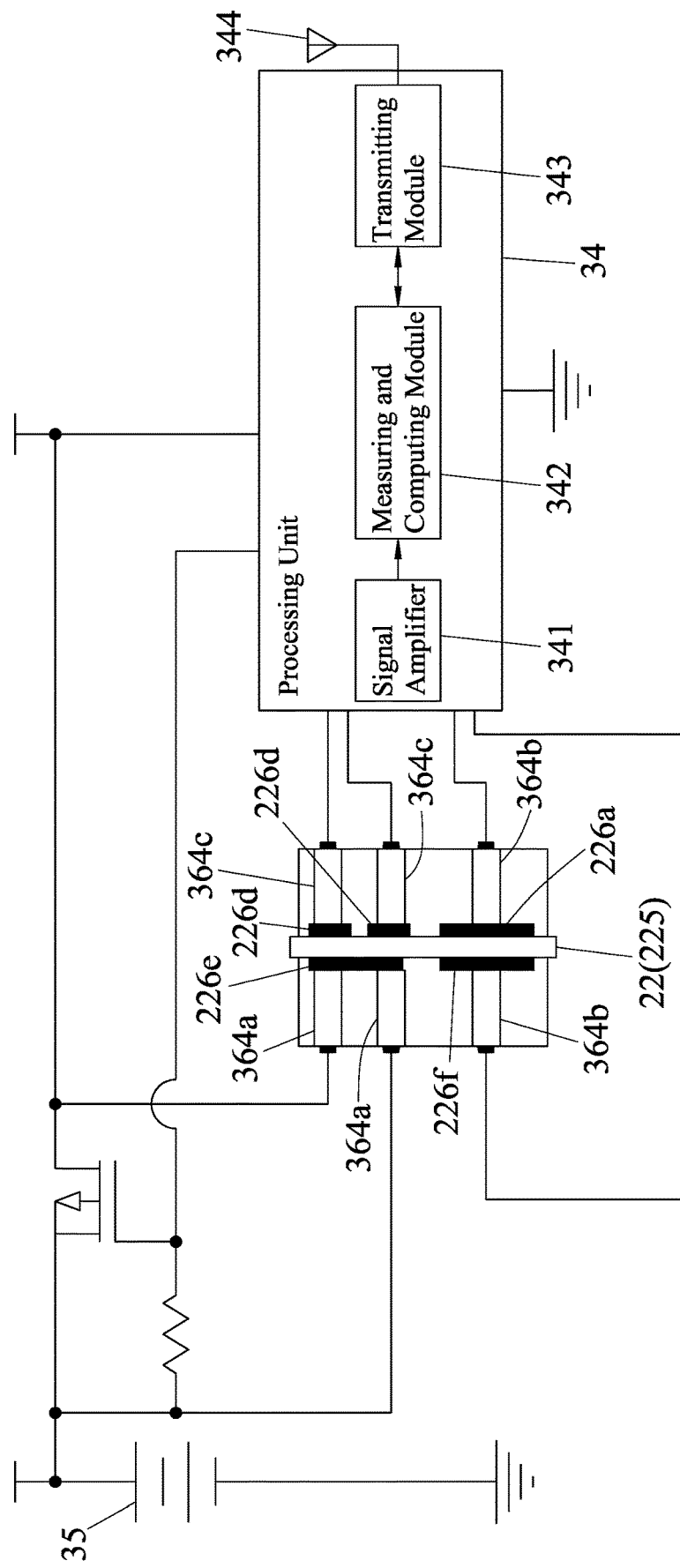

Referring to FIG. 13, in another modification of the sensing member 22 and the socket 36 of the first embodiment, the electrodes 226 of the sensing member include a working electrode 226a, a counter electrode 226f, a power-supplying electrode 226e, and two electrical contact sections 226d, and the number of the conducting members 364 of the transmitter 3 is six. The conducting members 364 are conducting coil springs and include two power-supplying conducting members 364a, two sensing conducting members 364b, and two transmitting conducting members 364c. When the sensing member 22 is inserted into the socket 367 of the connecting port 36, the power-supplying electrode 226e of the sensing member 22 is in contact with the power-supplying conducting members 364a to be electrically connected with the electrical contacts 331 of the circuit board 33. At the same time, each of the working and counter electrode 226a, 226f is in contact with a respective one of the sensing conducting members 364b to be electrically connected to the electrical contacts 331 of the circuit board 33, such that the processing unit 34 receives, processes, and sends the physiological signal to the external device. The electrical contact sections 226d are permitted to be respectively and electrically connected to the transmitting conducting members 364c.

Figure 14:
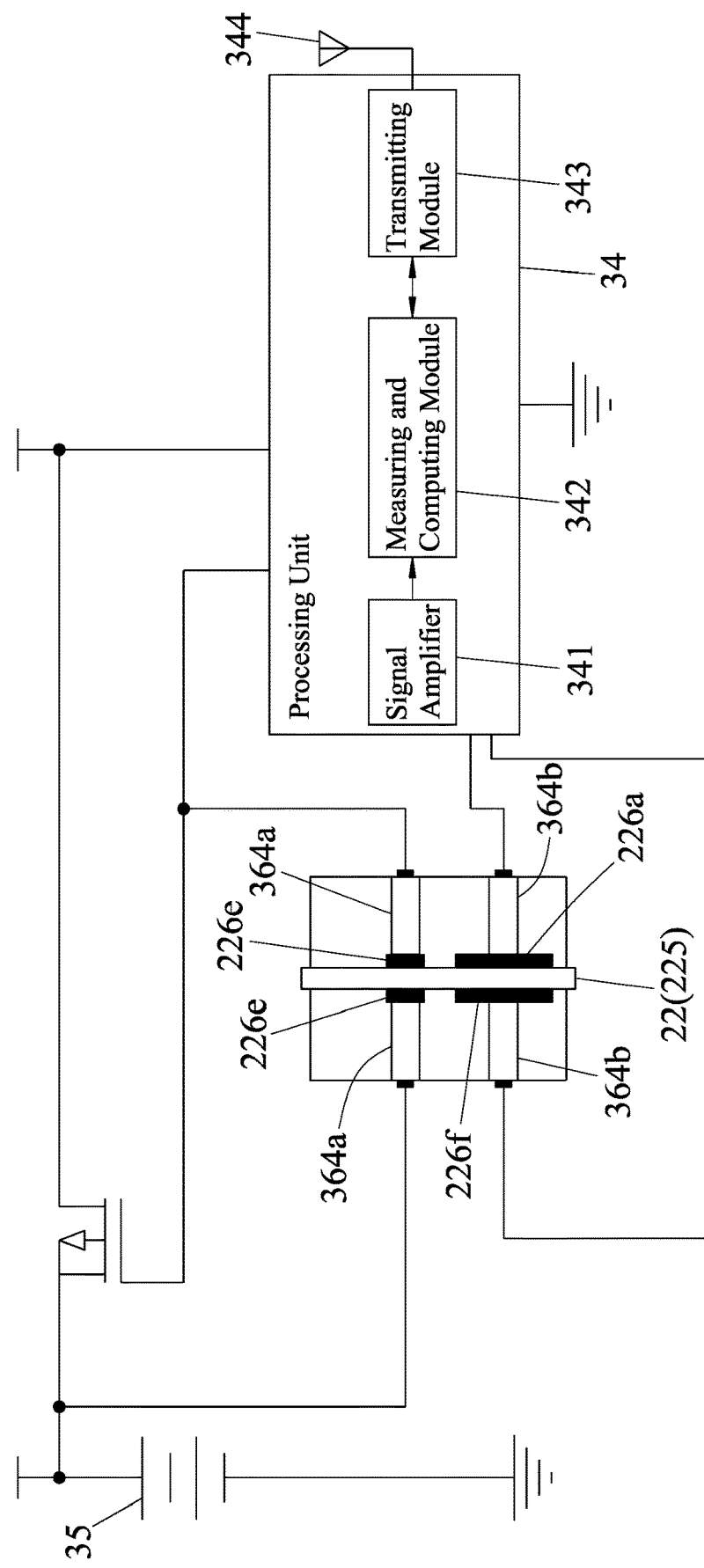

Referring to FIG. 14, in yet another modification of the sensing member 22 and the socket 36 of the first embodiment, the electrodes 226 of the sensing member include a working electrode 226a, a counter electrode 226f, and two power-supplying electrodes 226e, and the number of the conducting members 364 of the transmitter 3 is four. The conducting members 364 are conducting coil springs and include two power-supplying conducting members 364a and two sensing conducting members 364b. When the sensing member 22 is inserted into the socket 367 of the connecting port 36, the power-supplying electrodes 226e of the sensing member 22 are respectively in contact with the power-supplying conducting members 364a to be electrically connected with the electrical contacts 331 of the circuit board 33. At the same time, each of the working and counter electrode 226a, 226f is in contact with a respective one of the sensing conducting members 364b to be electrically connected to the electrical contacts 331 of the circuit board 33, such that the processing unit 34 receives, processes, and sends the physiological signal to the external device.

By utilizing the abovementioned modifications of the sensing member 22 and the socket 36 of the first embodiment, the electrical contacts 331 of the circuit board 33 and the electrodes 226 of the sensing member 22 are able to be electrically connected to activate the processing unit 34. It should be noted that the conducting coil springs in the abovementioned modifications may be conducting components of other forms.

In the above embodiments, the transmitter 3 is coupled to the biosensor 2 assembled on the base 1 wherein the base 1 is attached on the host skin.

Accordingly, the sensing member 22 of the biosensor 2 is inserted into the socket 367 of the transmitter 3 for the measurement of the analyte.

Overall, the first embodiment of the physiological signal monitoring device provides the following benefits:

1) The sensing member 22 is inserted into the transmitter 3 wherein each of the conducting members 364 bidirectionally contacts with the electrodes 226 of the sensing member 22 and the electrical contacts 331 of the circuit board 33 along directions of the first axis (D1) and the second axis (D2) respectively.

Therefore, the sensing member 22 is stably held within the socket 367 by the elastic conducting members 364 to provide reliable electric connection and signal transmission between the circuit board 33 and the sensing member 22.

2) In addition, the conducting members 364 could be the elastic coil conducting springs or the steel members complemented by the elastic members 369 to raise the tightness between the sensing member 22 and the circuit board 33 such that the reliable electric connection and signal transmission is provided. Due to the complementary assembly between the sensing member 22 and the socket 367, the vertical size of the device could be reduced. Furthermore, in this embodiment, because the conducting members 364 have high degree of freedom in the grooves 366, each of the conducting members 364 is forced to rotate relative to the grooves 366 during insertion of the sensing member 22 into the socket 367 and removal of the sensing member 22 from the socket 367, thereby reducing friction resistance between the socket 367 and the sensing member 22 and facilitating the reuse of the transmitter 3.

3) The battery 35 has not been turned on until the sensing member 22 is inserted into the socket 367 of the connecting port 36, thereby preventing from the power consumption before activating the physiological signal monitoring device. In addition, the socket 367 may be further adapted for the additional transmission device or a charging device to be inserted thereinto for data transmission and power charging respectively. Specifically, the power-supplying electrode of the charging device could be electrically connected with the electrical contacts 331 of the circuit board 33 through the power-supplying conducting members 364a for power charging; the electrical contact sections 226d of the additional transmission device could be electrically connected with the electrical contacts 331 of the circuit board 33 through the transmitting conducting members 364c for data transmission.

Figure 15:
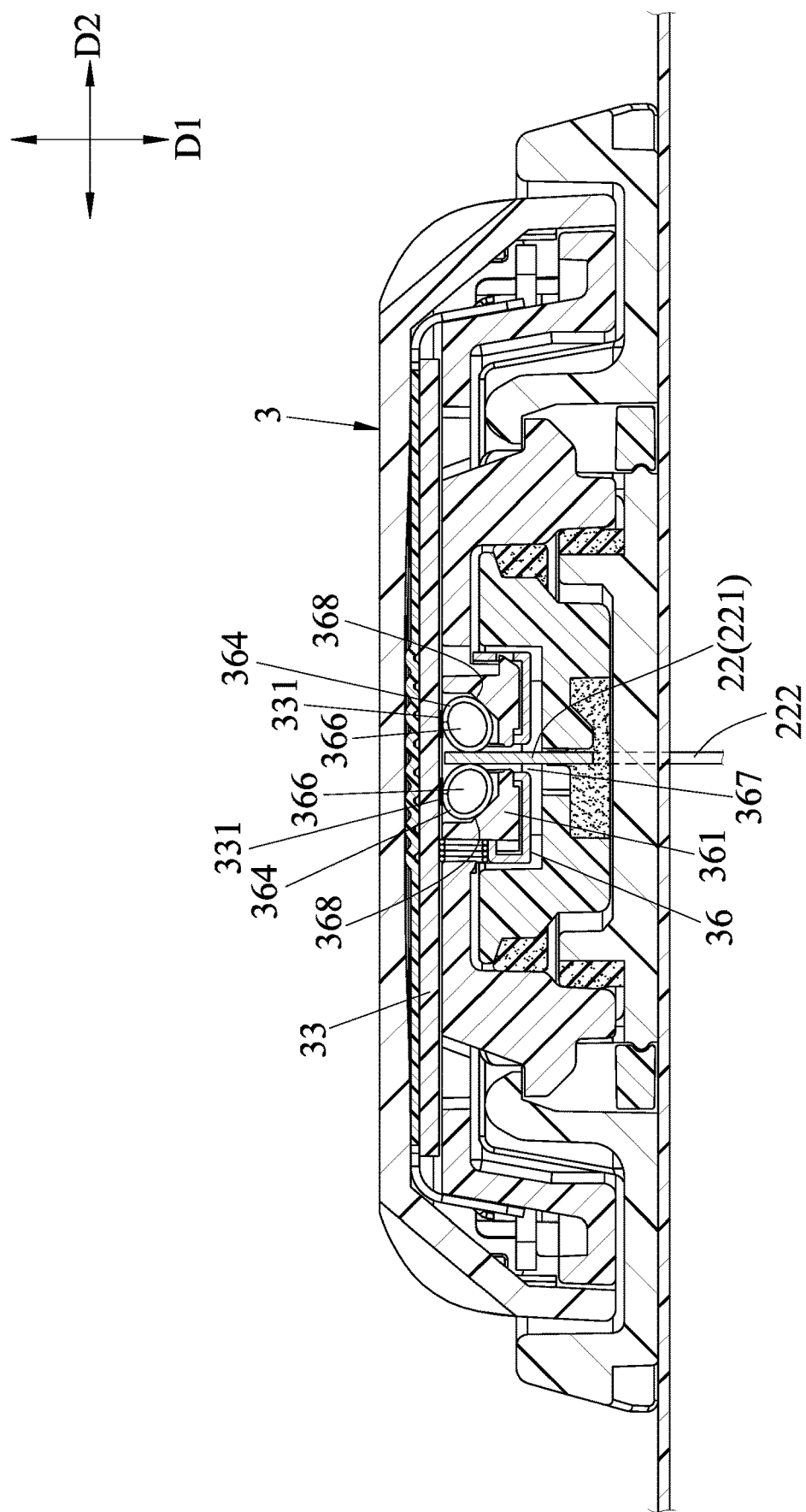
FIG. 15 is a fragmentary sectional view of a second embodiment of the physiological signal monitoring device.
Figure 16:
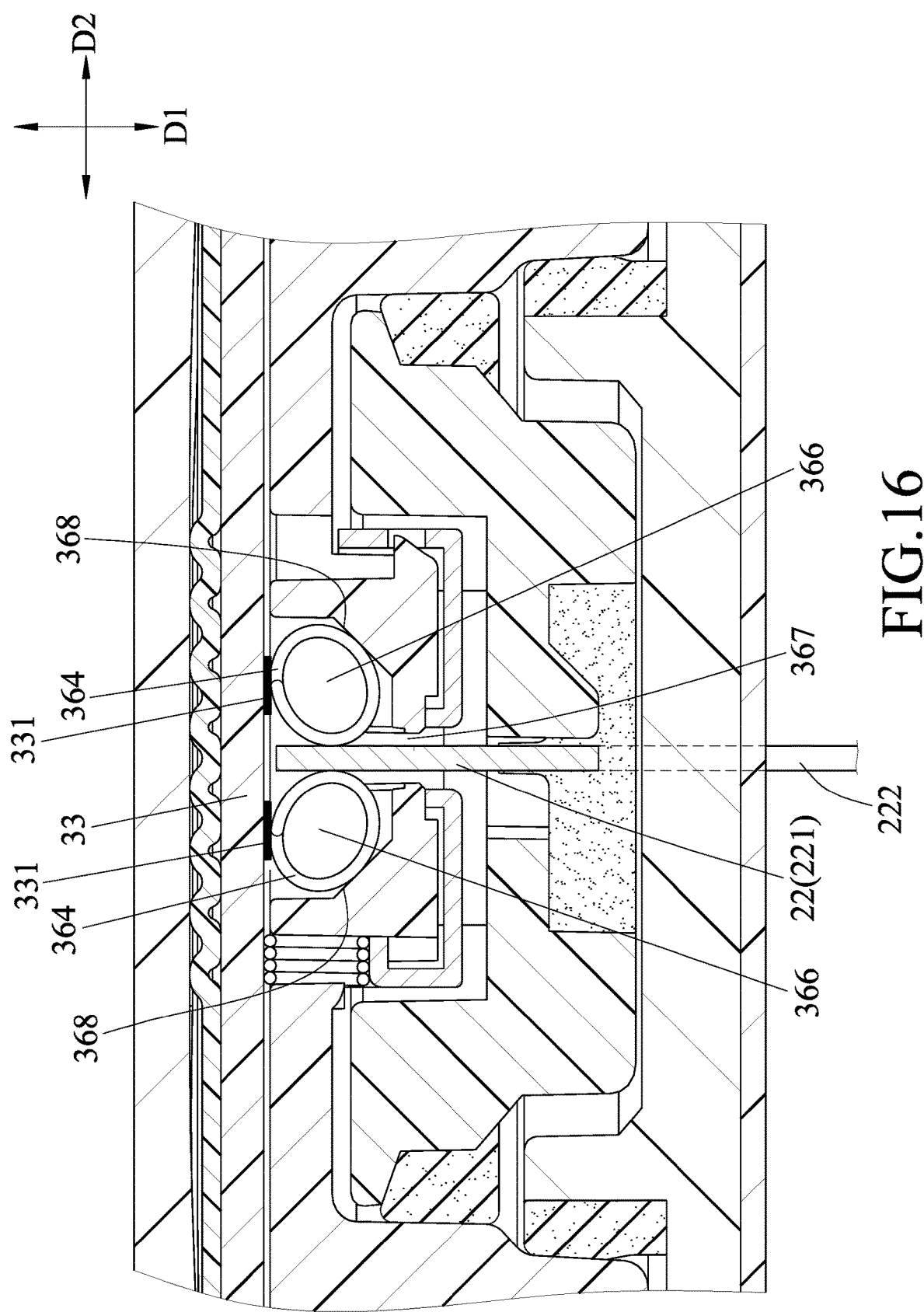
FIG. 16 is an enlarged view of FIG. 15.

FIGS. 15 and 16 illustrate a second embodiment of the physiological signal monitoring device wherein the difference between the first embodiment and the second embodiment is described as follows.

The port casing 361 of the connecting port 36 has a plurality of slanted surfaces 368 respectively disposed in the grooves 366 and facing the circuit board 33 and the sensing member 22. Therefore, the conducting members 364 are forced against the circuit board 33 and the sensing member 22 with force vector provided by the slanted surfaces 368 to ensure the contact therebetween and enhance the mobility of the conducting members 364. Moreover, the conducting members 364 could return to the predetermined position after the removal of the sensing member 22 from the socket 367 because of the slanted surfaces 368 such that the contact problem resulting in electric disconnection between the conducting member 364 and the sensing member 22 could be solved. In other embodiments, the conducting members 364 could be modified as hard components (ex. steel ball or steel ring) with the elastic members 369 configured between the conducting members 364 and the slanted surfaces 368.

Figure 17:
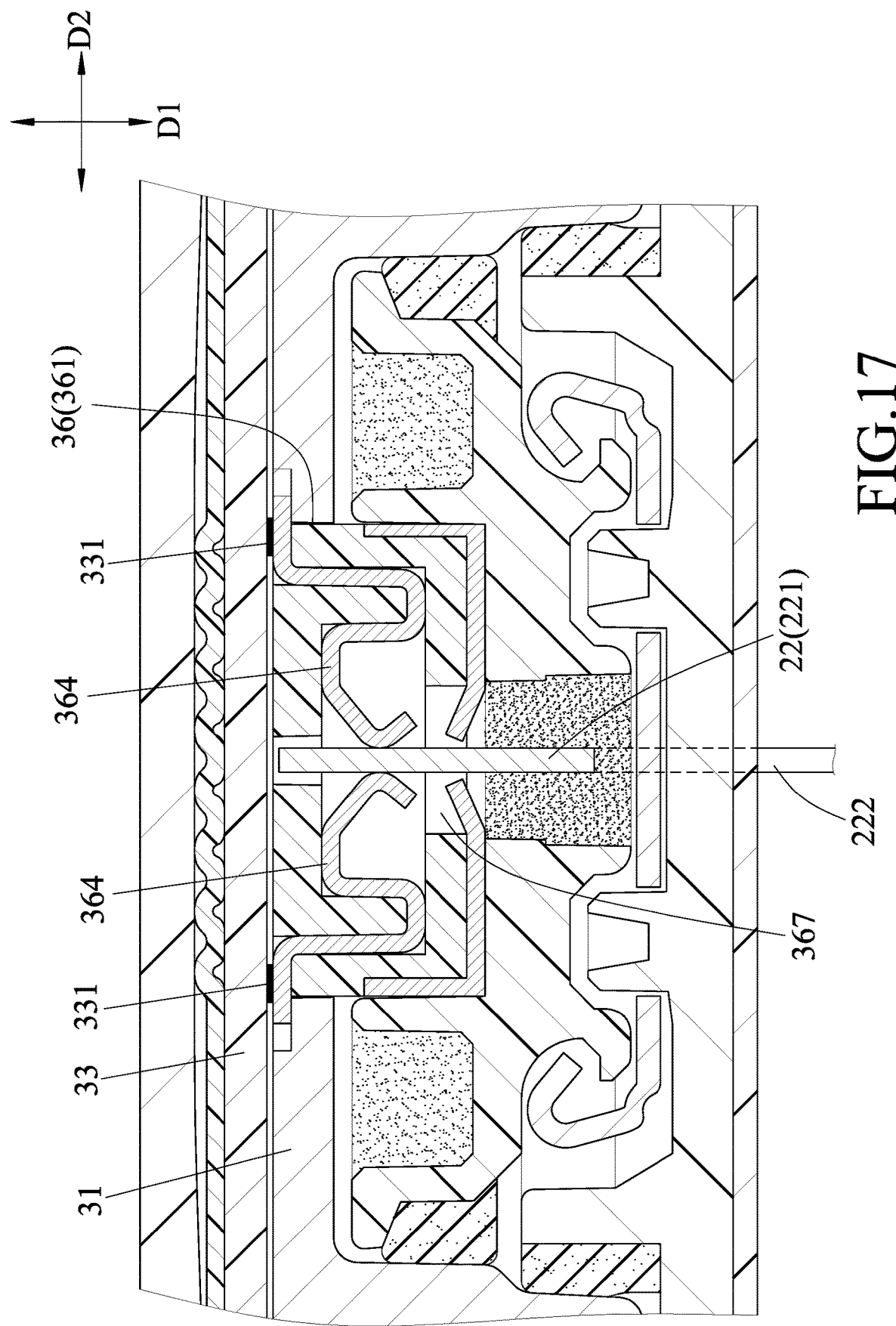
FIG. 17 is an enlarged fragmentary sectional view of a third embodiment of the physiological signal monitoring device.

FIG. 17 illustrates a third embodiment of the physiological signal monitoring device wherein the difference between the first embodiment and the third embodiment is described as follows.

In this embodiment, each of the conducting members 364 of the connecting port 36 is a leaf spring with one end contacted with the corresponding electrical contact 331 of the circuit board 33 along the first axis (D1) and another end contacted with the electrodes 226 of the sensing member 22 along the second axis (D2). Accordingly, the sensing member 22 is stably held within the socket 367 by the leaf springs 364 to provide reliable electric connection and signal transmission between the circuit board 33 and the sensing member 22.

Figure 18:
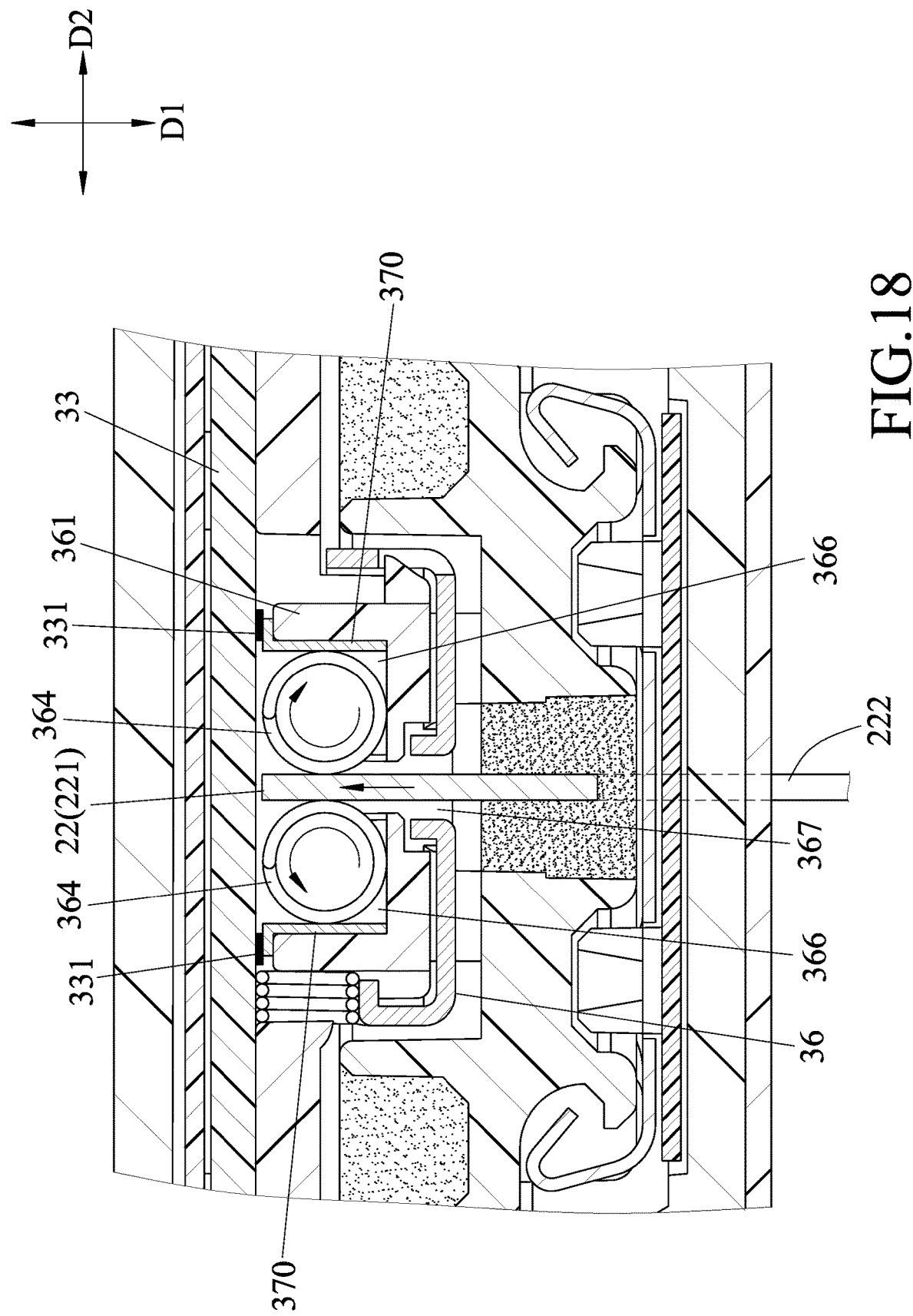
FIG. 18 is an enlarged fragmentary sectional view of a fourth embodiment of the physiological signal monitoring device.

FIG. 18 illustrates a fourth embodiment of the physiological signal monitoring device wherein the difference between the first embodiment and the fourth embodiment is described as follows.

The conducting members 364 are conducting coil springs. The connecting port 36 further includes a plurality of metal plates 370 respectively connected to the electrical contacts 331. In this embodiment, the metal plates 370 are welded to the electrical contacts 331 via surface mount technology (SMT), and extended toward the grooves 366 to be disposed between the port casing 361 and the conducting members 364. Therefore, each of the conducting members 364 coaxially contacted with a respective one of the metal plates 370 and the electrodes 226 of the sensing member 22 along an axis parallel to the second axis (D2) to provide reliable electric connection between the circuit board 33 and the sensing member 22.

Figure 19:
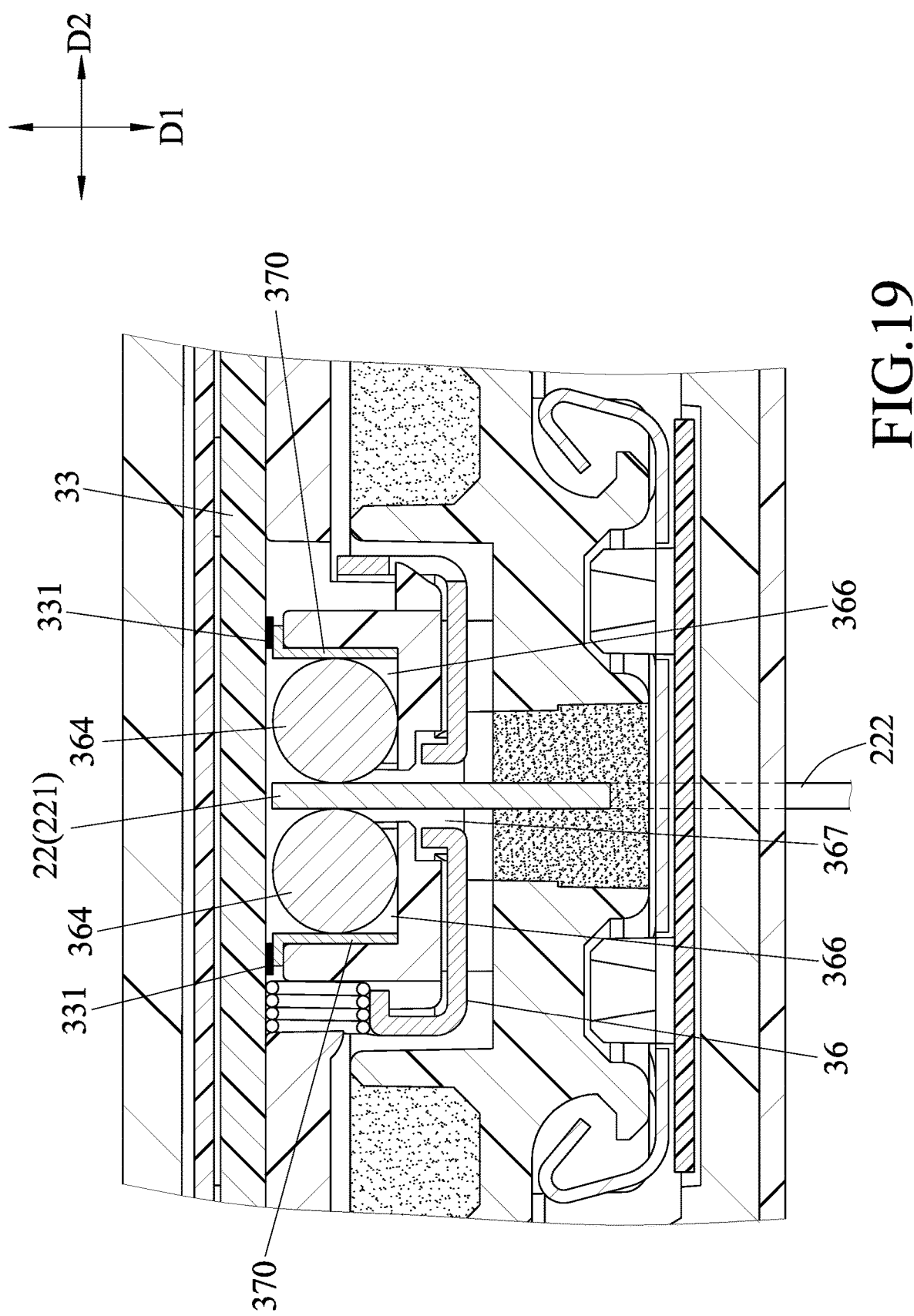
FIGS. 19 and 20 are enlarged fragmentary sectional views of various modifications of the fourth embodiment.
Figure 20:
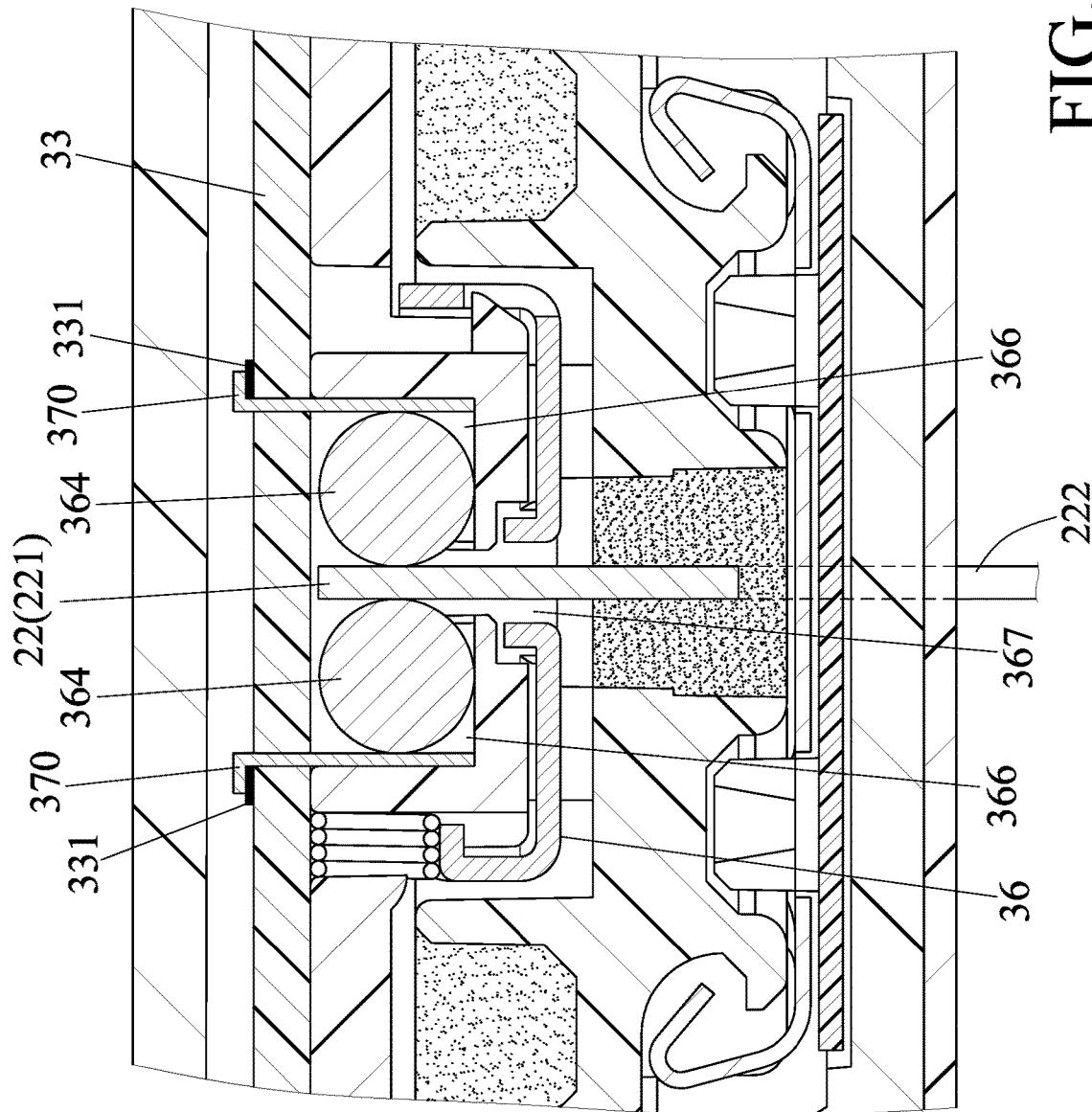
Figure 21:
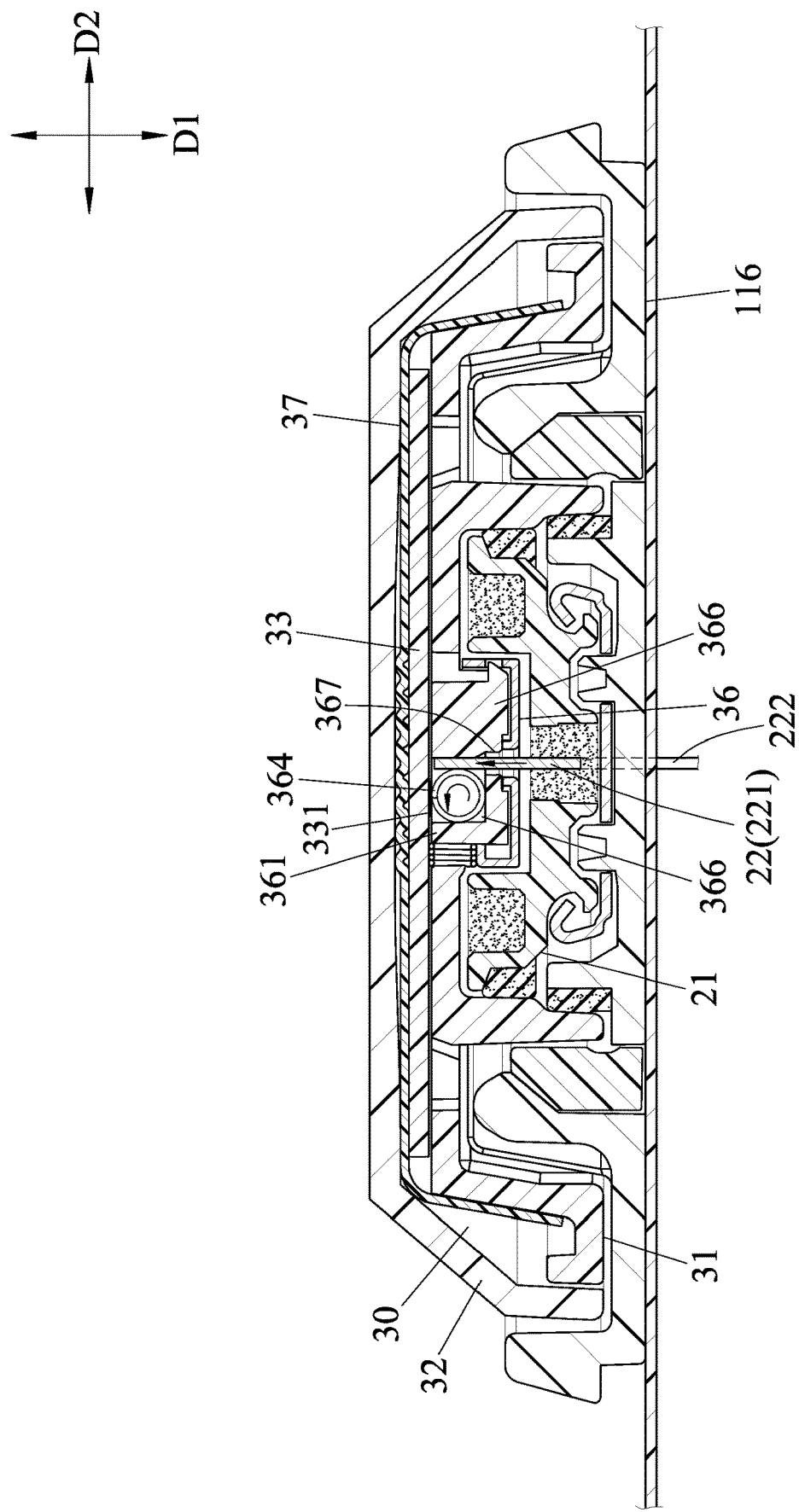
FIG. 21 is a fragmentary sectional view of still another modification of the first embodiment.
Figure 22:
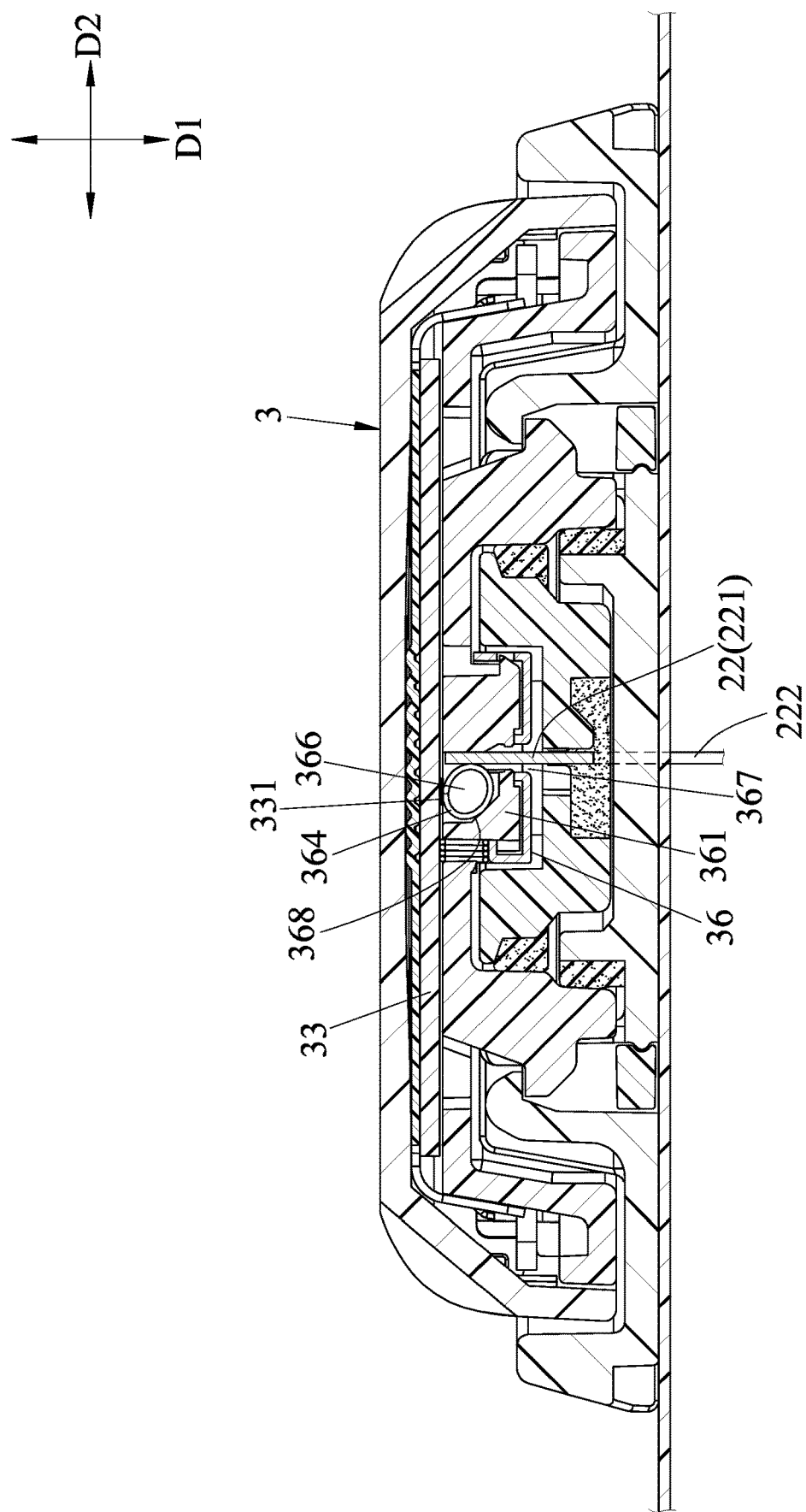
FIG. 22 is a fragmentary sectional view of a modification of the second embodiment.
Figure 23:
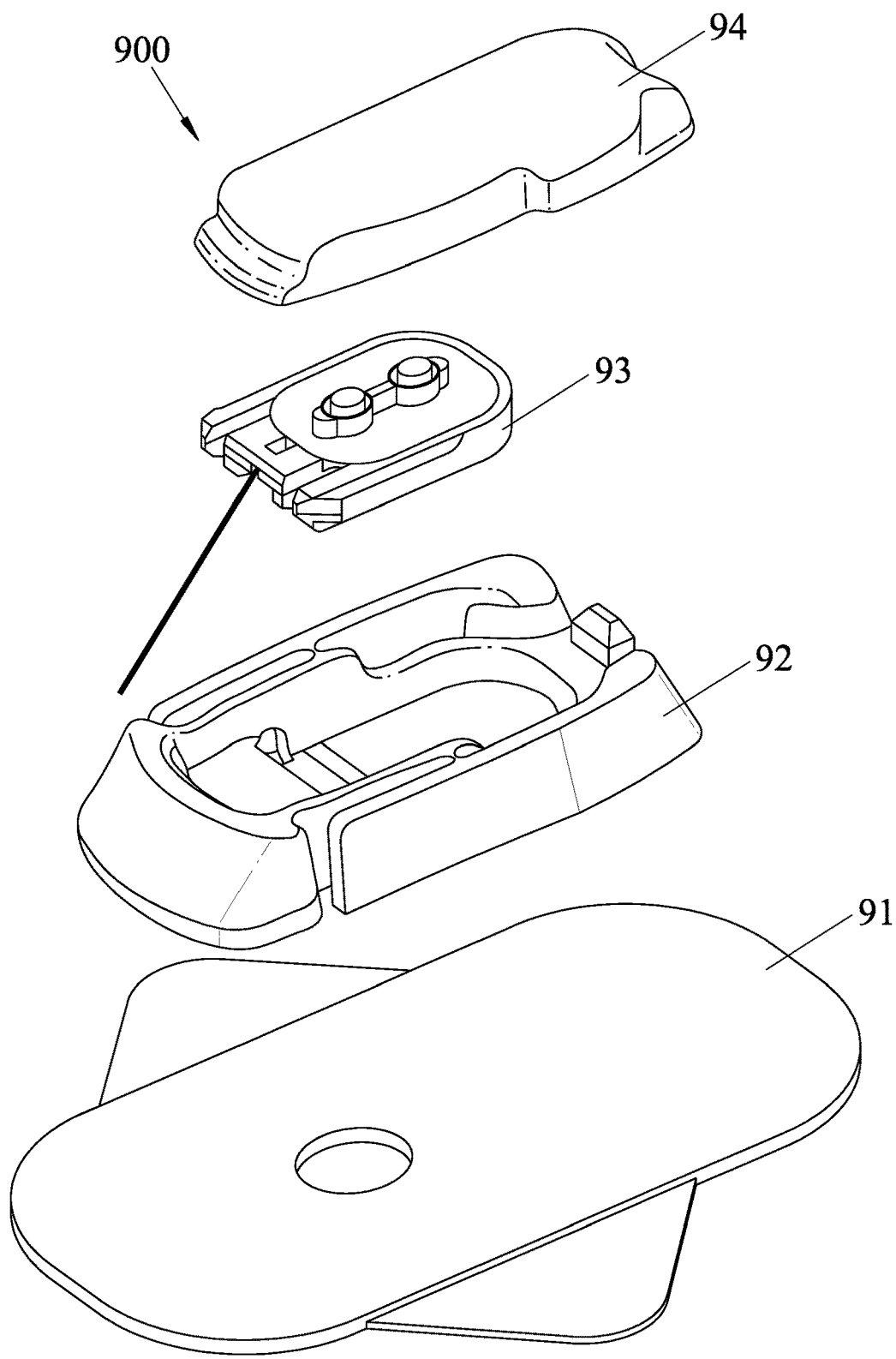
FIG. 23 is an exploded perspective view of a conventional sensing device.
Figure 24:
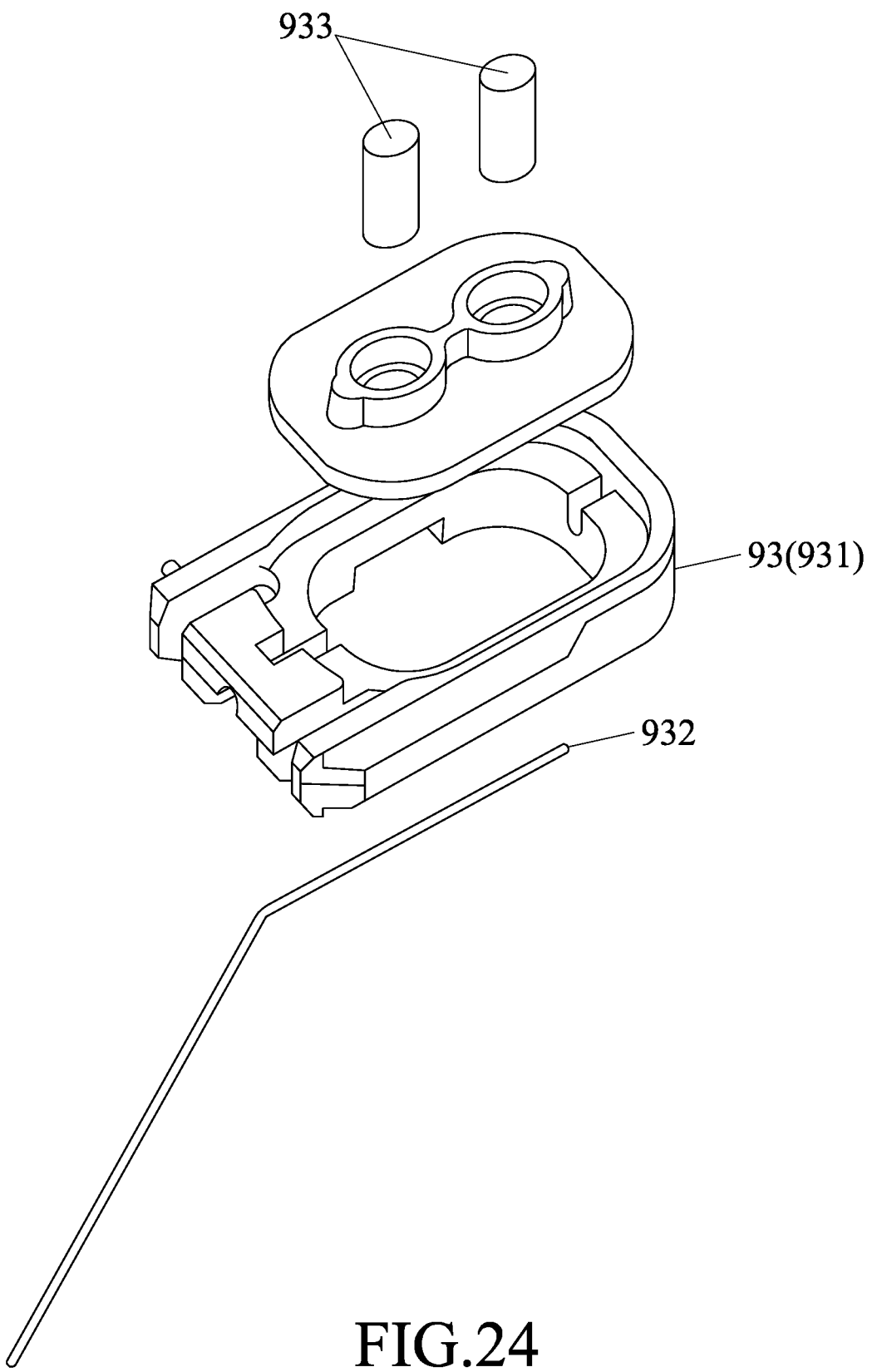
FIG. 24 is an exploded perspective view of a biosensor of the conventional sensing device.

FIGS. 19 and 20 illustrate other modifications of the fourth embodiment, in which the conducting members 364 are steel balls or steel rings instead wherein the metal plates 370 are welded to the electrical contacts 331 via surface mount technology (SMT) shown as FIG. 19 or dual in-line package (DIP) shown as FIG. 20. It should be noted that in the abovementioned embodiments, the conducting members 364 of the connecting port 36 are disposed at two opposite sides of the socket 367. However, in other embodiments, the conducting members 364 of the connecting port 36 can be disposed at single side of the socket 367 instead, such that only single side of the sensing member 22 is abutted against the conducting members 364. Referring to FIGS. 21 and 22, the sensing member 22 is stably held within the socket 367 by the elastic conducting members 364 and the port casing 361 to provide reliable electric connection between the circuit board 33 and the sensing member 22.

Consequently, the conducting members 364 are laterally configured at the socket 367 to contact with the electrodes 226 of the sensing member 22 and the electrical contacts 331 of the circuit board 33 after the transmitter 3 is coupled to the biosensor 2, thereby providing the reliable electric connection therebetween and holding of the sensing member 22. Moreover, the conducting members 364 are rotated relative to the grooves 366 during insertion or removal of the sensing member 22 from the socket 367 to reduce friction resistance between conducting members 364 and the sensing member 22 and facilitate the reuse of the transmitter 3. In addition, the conducting members 364 can be conducting coil springs, steel balls/rings with the elastic members 369 or metal plates 370 to provide bidirectional or coaxial connection between the sensing member 22 and the circuit board 33. Therefore, the electrodes 226 of various functions are electrically connected with the electrical contacts 331 of single connecting port 36 to activate the power supply, signal sensing and date transmission.

In addition to the embodiments described above, this disclosure further discloses a plurality of embodiments as defined by the claims, with each embodiment comprising the claim element(s) of the respective claim and the claim element(s) of any claim upon which the respective claim depends.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure. While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A physiological signal monitoring device for sensing a physiological signal in an analyte of a host, comprising:
    a sensing member including
        a signal sensing end adapted to be inserted underneath a skin of the host to sense the physiological signal, and
        a signal output end for outputting the physiological signal; and
    a transmitter connected to said sensing member for receiving, processing and transmitting the physiological signal, and including
        a circuit board having a plurality of electrical contacts, and
        a connecting port connected to said circuit board and having a socket which is communicated to said circuit board, and a plurality of steel balls which are received within said connecting port;
    wherein said sensing member is removably inserted into said socket;
    wherein each of said steel balls has one side electrically connected to a respective one of said electrical contacts of said circuit board and another side electrically connected to said signal output end of said sensing member for electric connection between the respective one of said electrical contacts and said signal output end;
    wherein, each of said steel balls is frictionally rotated by said sensing member during insertion of said sensing member into said socket and removal of said sensing member from said socket;
    wherein said steel balls of said connecting port are disposed at two opposite sides of said socket and
    wherein each of said steel balls has said one side contacted with the respective one of said electrical contacts along a direction of a first axis and said another side contacted with said signal output end along a direction of a second axis.

2. The physiological signal monitoring device as claimed in claim 1, wherein said connecting port further includes a port casing mounted on said circuit board and formed with said socket, and a plurality of grooves communicated to said socket to receive said steel balls therein.

3. The physiological signal monitoring device as claimed in claim 2, wherein said connecting port further includes a plurality of elastic members, each of said elastic members being mounted between said port casing and a respective one of said steel balls.

4. The physiological signal monitoring device as claimed in claim 1, wherein said connecting port further includes a plurality of metal plates respectively connected to said electrical contacts to force said steel balls against said sensing member, each of said steel balls coaxially contacted with a respective one of said metal plates and said signal output end of said sensing member.

5. The physiological signal monitoring device as claimed in claim 1, wherein said sensing member is inserted into said socket along the direction of the first axis, and said signal output end of said sensing member is electrically connected to each of said steel balls along the direction of the second axis.

* * * * *